US006835194B2

(12) United States Patent
Johnson et al.

(10) Patent No.: US 6,835,194 B2
(45) Date of Patent: Dec. 28, 2004

(54) IMPLANTABLE DEVICES AND METHODS FOR TREATMENT OF PAIN BY DELIVERY OF FENTANYL AND FENTANYL CONGENERS

(75) Inventors: Randolph Mellus Johnson, Half Moon Bay, CA (US); Felix Theeuwes, Los Altos Hills, CA (US); Edward M. Gillis, Cupertino, CA (US); Dana Litmanovitz, Sunnyvale, CA (US); Barbara Laidlaw, San Jose, CA (US); James Brown, Los Gatos, CA (US); John Culwell, San Francisco, CA (US); James A. Filice, Los Gatos, CA (US); Peter Wickman, San Francisco, CA (US); Su-Il Yum, Los Altos, CA (US); Andrew Poutiatine, Redwood City, CA (US); John Dinka, Fairfax, VA (US)

(73) Assignee: Durect Corporation, Cupertino, CA (US)

( * ) Notice: Subject to any disclaimer, the term of this patent is extended or adjusted under 35 U.S.C. 154(b) by 0 days.

(21) Appl. No.: 10/188,325

(22) Filed: Jun. 27, 2002

(65) Prior Publication Data

US 2003/0088236 A1 May 8, 2003

Related U.S. Application Data

(63) Continuation-in-part of application No. PCT/US01/43143, filed on Nov. 21, 2001, and a continuation-in-part of application No. PCT/US01/06955, filed on Mar. 2, 2001, and a continuation-in-part of application No. 09/522,535, filed on Mar. 10, 2000, now Pat. No. 6,541,021.

(60) Provisional application No. 60/377,541, filed on May 3, 2002, provisional application No. 60/323,406, filed on Sep. 17, 2001, provisional application No. 60/250,328, filed on Nov. 29, 2000, provisional application No. 60/188,263, filed on Mar. 10, 2000, and provisional application No. 60/125,589, filed on Mar. 18, 1999.

(51) Int. Cl.[7] .......................... A61K 9/22; A61M 11/00; A61M 3/00; A61F 13/00

(52) U.S. Cl. ................................. 604/890.1; 604/891.1; 604/93.01; 604/131; 604/132; 604/133; 424/422; 424/449

(58) Field of Search .......................... 604/890.1, 891.1, 604/93.01, 131–133; 424/422, 449

(56) References Cited

U.S. PATENT DOCUMENTS

| 3,141,823 A | 7/1964 | Janssen et al. |
| 3,760,984 A | 9/1973 | Theeuwes |
| 3,845,770 A | 11/1974 | Theeuwes et al. |
| 3,916,899 A | 11/1975 | Theeuwes et al. |

(List continued on next page.)

FOREIGN PATENT DOCUMENTS

WO     WO 97/27840     8/1997

(List continued on next page.)

OTHER PUBLICATIONS

Ahmedzai (1997), "New approaches to pain control in patients with cancer." *Eur. J. Cancer*, 33(6):S8–A14.

(List continued on next page.)

*Primary Examiner*—Thurman K. Page
*Assistant Examiner*—Isis Ghali
(74) *Attorney, Agent, or Firm*—Carol L. Francis; Bozicevic, Field & Francis LLP; Tom McCracken

(57) ABSTRACT

The invention features devices and methods for treatment of pain. The drug delivery device is a drug delivery system adapted for whole implantation in a subject and to provide pain relief by delivery of fentanyl or a fentanyl congener (e.g., sufentanil) over a protracted period of time (e.g., at least 3 days or more than 3 days). The device comprises a housing defining a reservoir that contains a drug formulation, a pump operatively connected to the housing so as to facilitate movement of drug out of the reservoir and out of the device, and a thermal expansion element which defines a flow pathway comprising a thermal expansion channel to accommodate thermal expansion of formulation in the reservoir. The device can further comprise a valve positioned within the flow pathway so as to prevent movement of drug out of the reservoir prior to use.

27 Claims, 13 Drawing Sheets

U.S. PATENT DOCUMENTS

| | | |
|---|---|---|
| 3,923,426 A | 12/1975 | Theeuwes |
| 3,987,790 A | 10/1976 | Eckenhoff et al. |
| 3,995,631 A | 12/1976 | Higuchi et al. |
| 3,998,834 A | 12/1976 | Janssen et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |
| 4,167,574 A | 9/1979 | Janssens |
| 4,203,440 A | 5/1980 | Theeuwes |
| 4,203,442 A | 5/1980 | Michaels |
| 4,210,139 A | 7/1980 | Higuchi |
| 4,327,725 A | 5/1982 | Cortese et al. |
| 4,360,019 A | 11/1982 | Portner et al. |
| 4,487,603 A | 12/1984 | Harris |
| 4,576,951 A | 3/1986 | Rovati et al. |
| 4,582,835 A | 4/1986 | Lewis et al. |
| 4,588,580 A | 5/1986 | Gale et al. |
| 4,627,850 A | 12/1986 | Deters et al. |
| 4,681,560 A | 7/1987 | Schulte et al. |
| 4,692,147 A | 9/1987 | Duggan |
| 4,725,852 A | 2/1988 | Gamblin et al. |
| 4,769,372 A | 9/1988 | Kreek |
| 4,781,924 A | 11/1988 | Lee et al. |
| 4,865,845 A | 9/1989 | Eckenhoff et al. |
| 5,057,318 A | 10/1991 | Magruder et al. |
| 5,059,423 A | 10/1991 | Magruder et al. |
| 5,112,614 A | 5/1992 | Magruder et al. |
| 5,137,727 A | 8/1992 | Eckenhoff |
| 5,180,716 A | 1/1993 | Yaksh et al. |
| 5,187,177 A | 2/1993 | Garzaran |
| 5,234,692 A | 8/1993 | Magruder et al. |
| 5,234,693 A | 8/1993 | Magruder et al. |
| 5,346,903 A | 9/1994 | Ackerman et al. |
| 5,356,635 A | 10/1994 | Raman et al. |
| 5,451,408 A | 9/1995 | Mezei et al. |
| 5,472,943 A | 12/1995 | Crain et al. |
| 5,486,362 A | 1/1996 | Kitchell et al. |
| 5,487,739 A | 1/1996 | Aebischer et al. |
| 5,512,578 A | 4/1996 | Crain et al. |
| 5,580,876 A | 12/1996 | Crain et al. |
| 5,589,480 A | 12/1996 | Elkhoury et al. |
| 5,633,000 A | 5/1997 | Grossman et al. |
| 5,660,854 A | 8/1997 | Haynes et al. |
| 5,672,167 A | 9/1997 | Athayde et al. |
| 5,728,396 A | 3/1998 | Peery et al. |
| 5,729,396 A | 3/1998 | Dudley et al. |
| 5,747,058 A | 5/1998 | Tipton et al. |
| 5,767,125 A | 6/1998 | Crain et al. |
| 5,798,114 A | 8/1998 | Elsberry et al. |
| 5,858,388 A | 1/1999 | Grossman et al. |
| 5,861,248 A | 1/1999 | Russell et al. |
| 5,866,164 A | 2/1999 | Kuczynski et al. |
| 5,980,927 A | 11/1999 | Kuczynski et al. |
| 5,985,305 A | 11/1999 | Peery et al. |
| RE36,547 E | 2/2000 | Crain et al. |
| 6,096,756 A | 8/2000 | Crain et al. |
| 6,203,813 B1 | 3/2001 | Gooberman |
| 6,245,351 B1 | 6/2001 | Nara et al. |
| 6,395,292 B2 | 5/2002 | Peery et al. |
| 6,436,091 B1 | 8/2002 | Harper et al. |

FOREIGN PATENT DOCUMENTS

| | | |
|---|---|---|
| WO | WO 97/49391 | 12/1997 |
| WO | WO 98/51246 A | 11/1998 |
| WO | WO 99/36071 | 7/1999 |
| WO | WO 00/54745 A2 | 9/2000 |

OTHER PUBLICATIONS

Anderson et al., (1998), "Alternate routes of opioid administration in palliative care: pharmacologic and clinical concerns." *J. Pharmaceut. Care Pain Sympt. Control*. 6:5–21.

Bansinath, et al., (1989), "Hyperglycemia does not modify the pupillary effects of $\mu$ and κ opiate agonists in mice" *J. Ocular Pharmacology*, vol. 5(1): 33–43.

Bruera et al., (1987), "Use of the subcutaneous route of the administration of narcotics in patients with cancer pain" *Cancer*, vol. 62(2): 407–411.

Cherny et al . (1995). "Opioid pharmacotherapy in the management of cancer pain" *Cancer*, vol. 76(7): 1283–1293.

Clotz et al. (1991). "Clinical uses of fentanyl, sufentanil, and alfentanil" *Clinical Pharmacy*, vol. 10. 581–593.

Coda et al . . . (1997). "Comparative efficacy of patient–controlled administration of morphine, hydromorphone, or sufentanil for the treatment of oral mucositis pain following bone marrow transplantation" *Pain*, vol. 72: 333–346.

Coyle et al . . . (1994), "Subcutaneous opioid infusions at home." *Oncology*, 8 21–27.

Crane (1994). "Intermittent subcutaneous infusion of opioids in hospice home care: An affective, economical, manageable option" *Am. J. Hospice & Palliative care*, vol. Jan./Feb.: 8–12.

Chasmana et al . . . (1987) "Gastrointestinal transit following inthrathecal or subcutaneous narcotic analgesies" *Arch. Int. Pharmacodyn.*, vol. 286: 152–161.

Fine (1997), "Fentanyl in the treatment of cancer pain," *Sem. Oncol.*, 24(16) S16–S27.

Finley (1990), "Pain management with spinally administered opioids." *Am J. Hosp. Pharm* , 47(1):S14–S17.

Funinaga et al . . . (1988). "Reproductive and teratogenic effects of sufentanil and alfentanil in Sprague–Dawley rate" *Anesth Analg*. vol. 67: 166–169.

Geller et al . . . (1993). "A randomized double–blind comparison of epidural sufentanil versus intravenous sufentanil or epidural fentanyl analgesia after major abdominal surgery" *Anesth Anallg*. vol. 76: 1243–1250.

Jeal et al . . . (1997), "Transdermal fentanyl A review of its pharmacologic properties and therapeutic efficacy in pain control." *Drugs*, 53:109–138.

Kerr et al . . . (1988), "Continuous narcotic infusion with patient–controlled analgesia for chronic cancer pain in out-patients." *Ann. Intern. Med.*, 108:554–557.

Kingery (1997), "A critical review of controlled clinical trials for peripheral neuropathic pain and complex regional pain syndromes." *Pain*, 73:123–139.

Leelanuntakit (1996), "Management of cancer–related pain with transdermal fentnyl" *J. Med Assoc. Thai*, vol. 79)6):341–346.

Manin et al . (1983), "Epidural and intrathecal narcotics." *Can. Anaesth Soc J*, 30 662–673.

Moulin et al . . . (1992) "Subcutaneous narcotic infusions for cancer pain treatment outcome and guidelines for use" *Can. Med. Assoc. J.*, vol. 146(6), 891–897.

Mucha et al . . . "Parket and Radow test of drug withdrawal aversion opposite effect in rats chronically infused with sufentanil or amphelamic" *Pharmacology Biochem. & Behavior*. vol. 35: 219–224.

Paix et al . . . (1995), "Subcutaneous fentanyl and sufentanil infusion substitution for morphine intolerance in cancer pain management" *Pain* , vol. 3: 263–269.

Satterlee (1991). "Ctiteria for use of fentanyl citrate, sufentanil citrate, and alfentanil hydrochloride" *Clinical Pharmacy*. vol. 10: 635–637.

Shaw (1993), "Treatment of intractable cancer pain by electronically controlled parenteral infusion of analgesic drugs." *Cancer*, 72:3416–3425.

Skaer (1993), "Management of pain in the cancer patient." *Clin. Ther.*, 15:638–649.

Slattery et al . . . (1985), "Newer methods of delivery of opiates for relief of pain." *Drugs 30:539–551*.

Sjøgren et al . . . (1994), "Disappearace of morphine–induced hyperalgesia after discontinuing or substituting morphine with other opioid agonists" *Pain*, vol. 59: 313–316.

Taverne et al . . . (1992). "Comparative absorption and distribution pharmacokinetics of intravenous and epidural sufentanil for major abdomincal surgery" *Clin. Pharmacokinet*, vol. 23(3): 231–237.

Van den Hoogen et al . . . (1987). "Epidural and subcutancous morphine, meperidine (pethidine), fentanyl and sufentanil in the rat: Analgesia and other *in vivo* pharmacologic effects" *Anesthesiology*, vol. 66: 186–194.

Van den Hoogen et al . (1988) "Respiratory effects of epidural and subcutaneous morphine, meperdine (pethidine), fentanyl and sufentanil in the rat" *Anesth Analg*, vol. 67 1071–1078.

Vertafridda et al . . . (1987), "Intraspinal morphine for cancer pain." *Acta Anaesthesiol Scand.*, 31(85):47–53.

Wagner et al . . . (1997) "Pharmacokinetics and pharmacodynamics of sedatives and analgesicics in the treatment of agitated critically ill patients" *Clin. Pharmacokinet*. vol. 33(6): 426–453.

Willens et al . . . (1993). "Pharmacodynamics, pharmacokinetics, and clinical uses of fentanyl, sufentanil, and alfentanil" *Heart & Lung*, vol. 22(3): 239–251.

Zeiler et a . . . (1991), "Kontinuierliche peridurale sufentanil–applikation zur postoperativen analgesic" *Anaesthesisi*. vol. 40: 543–548.

IMPLANTABLE DEVICES AND METHODS FOR TREATMENT OF PAIN BY DELIVERY OF FENTANYL AND FENTANYL CONGENERS

CROSS-REFERENCE TO RELATED APPLICATIONS

This application is a continuation-in-part of:

U.S. application Ser. No. 09/522,535, filed Mar. 10, 2000, now U.S. Pat. No. 6,541,021, which application claims the benefit of U.S. provisional application Ser. No. 60/125,589, filed Mar. 18, 1999;

PCT application Ser. No. PCT/US01/06955, filed Mar. 2, 2001, which application claims the benefit of U.S. provisional application Ser. No. 60/188,263, filed Mar. 10, 2000; and PCT application serial no. PCT/US01/43143, filed Nov. 21, 2001, which application claims the benefit of U.S. provisional application Ser. No. 60/250,328, filed Nov. 29, 2000;

and this application further claims the benefit of U.S. provisional application Ser. No. 60/323,406, filed Sep. 17, 2001; and the benefit of U.S. provisional application No. 60/377,541, filed May 3, 2002;

each of which applications is hereby incorporated by reference in its entirety.

FIELD OF THE INVENTION

The invention relates to devices and methods for the management of pain. Particularly, the invention relates to an implanted drug delivery device used to deliver a potent pain-killing drug over a protracted period of time.

BACKGROUND OF THE INVENTION

Many medications are used for the treatment of pain, ranging from well known, over-the-counter compounds such as aspirin, acetaminophen, ibuprofen and other non-steroidal anti-inflammatory compounds to the newly developed chemical entities such as the cyclooxygenase II inhibitor compounds. Opiates in various forms, including opium, heroine and morphine which derive from the opium poppy, have very powerful analgesic properties. Opiates have been widely used for anesthesia as well for the treatment of pain, especially where the pain is very severe. In addition to these natural opiates, many synthetic opioids have since been synthesized including methadone, fentanyl and congeners of fentanyl such as sufentanil, alfentanil, lofentanil, carfentanil, remifentanil, etc. Of the opioids, morphine is still the drug of choice for management of pain at least in part due to its low cost, the ability of the drug to provide relief from pain of a variety of origins, and the vast experience with this drug. Despite its therapeutic advantages and vast experience with the drug, many pain management experts believe that morphine and other opioids are under-prescribed for patients who require long-term pain therapy.

One reason for underprescription is the risk of the side effects associated with long-term administration of opioids in general, such as development of opiate tolerance, dependence, constipation, and/or other undesirable side effects (see, e.g., Moulin et al. 1992 Can Med. Assoc. J. 146:891–7). Patients who develop opioid tolerance require increased doses to achieve a satisfactory analgesic effect, and risk the development of further undesirable side effects such as respiratory depression, which can be life threatening. Physical dependence, which is related to factors such as the dose administered and the length of the administration period, can generally only be resolved by discontinuing opioid administration, which in turn results in the onset of severely painful withdrawal symptoms. Other side effects that can be associated with administration of opioids include reduced cough reflex, bronchial spasms, nausea, vomiting, peripheral vasodilation, orthostatic hypotension, vagal impact on the heart, contraction of smooth muscles (sphincters), reduced peristaltic motility in the gastrointestinal tract (e.g., constipation), urinary retention, changes in regulation of body temperature and sleep pattern, and release of histamine, adrenalin, and anti-diuretic hormone. The negative effects on respiratory function especially impact postoperative patients, who are particularly susceptible to depression of respiratory function. Even where the concerns regarding side effects might be outweighed by the serious need for pain relief as in terminally ill patients, many doctors still avoid prescribing opioids due to concerns of abuse of surplus medication by others in contact with the patient, or even that their frequent prescription of the drug might lead to criminal investigation.

In addition to the disadvantages listed above pertaining to opioids in general, morphine itself has also been associated with particular side effects, at times so severe as to make such therapy intolerable, especially for patients who are on long-term pain therapy or who require high doses of medication to obtain relief. Some of these side effects associated with morphine usage, particularly at high doses, include nausea and vomiting (see for example Paix et al. (1995) *Pain* 63:263–9) and severe constipation. In addition, Sjorgen et al. (1994 *Pain* 59:313–316) have reported the phenomena of hyperalgesia (increased response to certain stimulus which is not normally painful), allodynia (sensation of pain felt even when stimulus is not normally painful) and myoclonus associated with morphine use. It has been hypothesized that morphine and its metabolites may induce such abnormal sensitivity (see, e.g., Sjorgen et al. (1994) *Pain* 59:313–316).

Fentanyl and its congeners were originally developed as anesthesia agents, and are generally used in the United States for the limited purposes of intravenous administration in balanced general anesthesia, as a primary anesthetic, or, in the case of sufentanil, for epidural administration during labor and delivery. However, these drugs also have powerful analgesic properties and are several hundred or thousand times more potent than morphine depending on the particular congener. A few studies have in fact suggested that fentanyl and its congeners be used instead of morphine due to their increased potency and decreased side effects relative to morphine (see e.g., Sjorgen et al. (1994) *Pain* 59:313–316 and Paix et al. (1995) *Pain* 63:263–9). Fentanyl and its congeners are, however, more difficult to administer than morphine since they are not orally absorbed, are extremely potent (requiring very precise, accurate dosing of small amounts) and have very short half lives in the body thus requiring frequent dosing. For these reasons, conventional methods for delivery of opioid analgesics are inadequate to meet these delivery requirements. For example, fentanyl has been administered in single, small intravenous doses, but this method of administration, besides being impractical for long-term therapy, results in a short duration of action and rapid recovery due to a redistribution into fat stores and a rapid decline in plasma concentration. The development of transdermal patch delivery technology allowed fentanyl to be delivered continuously through the skin (e.g., the commercial Duragesic™ transdermal patch). Since the transdermal delivery method provided for constant drug delivery, it was a marked improvement relative to bolus injection;

however, transdermal delivery also has several limitations. For example, transdermal delivery is disadvantageous in that the dose of drug that can be delivered is limited by the available skin surface area, thus making transdermal delivery suitable for low-to-medium opioid dose requirements, but often inadequate for more high dose requirements. In addition, transdermal delivery of drug is disadvantageous in that there is a delay in obtaining steady state plasma concentrations upon initiation of therapy, as well as a prolonged period of continued effect even after removal of the patch. Other problems associated with transdermal delivery include skin irritation, loss of adhesion after exposure to moisture (e.g., perspiration, bathing) the potential for diversion of drug for illicit purposes and patient distaste for the unsightliness of highly visible patches.

While subcutaneous infusion of fentanyl and sufentanil have been the subject of experimentation on a limited basis, the methods disclosed in the prior art are impractical as long-term pain therapies. Paix et al. (1995 *Pain* 63:263–9), for example, discloses the use of subcutaneous fentanyl and sufentanil as an alternative therapy in a small number of patients who suffered significant side effects associated with administration of morphine. In Paix et al., the drug was infused into the subcutaneous space in relatively low drug concentrations and at relatively large volume rates (e.g., on the order of 3 mL/day to 40 mL/day) via an external syringe driver. The treatment method disclosed by Paix et al. has several major disadvantages that render it impractical for long-term therapy. First, the provision of drug from an external source adversely affects mobility of the patient and is therefore inconvenient for ambulatory patients, increases the risk of infections at the subcutaneous delivery site and provides an opportunity for drug to be diverted for illicit uses. Second, the infusion of large volumes of fluid may result in tissue damage or edema at the site of infusion. In addition, the absorptive capacity of the subcutaneous space limits the volume of fluid that can be delivered (see, e.g., Anderson et al., supra), and this volumetric limitation can in turn limit the amount of drug that can be administered (e.g., in Paix et al., more potent opioids were administered to some patients requiring high doses since the volume of morphine required was too large to be effectively absorbed in the subcutaneous tissues).

As is evident from the above, there is a great need for devices and methods for effective and practical management of pain, particularly pain of long duration, with better efficacy and reduced side effects. The present invention addresses this problem.

SUMMARY OF THE INVENTION

The invention features devices and methods for treatment of pain. The drug delivery device is a controlled drug delivery system adapted for whole implantation in a subject and to provide pain relief by delivery of fentanyl or a fentanyl congener (e.g., sufentanil) over a protracted period of time (e.g., at least about 3 days or more than about 3 days). The device comprises a housing defining a reservoir that contains a drug formulation, a pump operatively connected to the housing so as to facilitate movement of drug out of the reservoir and out of the device, and a thermal expansion element which defines a flow pathway comprising a thermal expansion channel to accommodate thermal expansion of formulation in the reservoir. The device can further comprise a valve positioned within the flow pathway so as to prevent movement of drug out of the reservoir prior to use.

Accordingly, in one aspect the invention features a controlled drug delivery device, adapted for whole implantation, the device comprising a housing defining a reservoir, the reservoir containing a formulation comprising a drug selected from the group consisting of fentanyl or a fentanyl congener, wherein the drug is present in an amount sufficient for treatment of pain in a subject for a period of at least about 3 days; a pump operatively connected to the housing; and a thermal expansion element comprising an inlet, a thermal expansion channel adapted to contain a volume of formulation associated with thermal expansion. In use, the inlet, thermal expansion channel, and outlet define a flow pathway from the reservoir and out of the device such that actuation of the pump effects movement of formulation through the flow pathway.

In specific embodiments, the thermal expansion element comprises a flow pathway that is at least partially defined by a plug, which plug can be seated within the housing. In other embodiments the thermal expansion element comprises a flow pathway is at least partially defined by a plug seated within the device housing, and by the plug and an inner wall of the housing.

In further specific embodiments, the thermal expansion element comprises a valve positioned and adapted for maintaining a sealed reservoir until opened. In related embodiments, the thermal expansion element comprises a plunger, the plunger having at least a portion slidably positioned within the flow pathway and having a portion seated within the valve such that when in a closed position the plunger and valve occlude the flow pathway to prevent movement of formulation out of the outlet.

In further specific embodiments, the flow pathway narrows from a wider inlet and thermal expansion channel to a narrower outlet.

In still further embodiments, the device is adapted for delivery of drug at a rate of from about 0.01 micrograms per hour to 2000 micrograms per hour.

In another embodiment, the drug in the formulation in the reservoir is present in a concentration of about 5 mg/mL to about 400 mg/mL.

In an embodiment of particular interest, the drug is sufentanil.

In another aspect, the invention features a method of treating pain in a subject, the method comprising wholly implanting at an implantation site in a subject a drug delivery device as described above, and parenterally delivering the formulation from the drug delivery device to the subject so that drug enters the systemic circulation and is transported thereby to a site of action in an amount sufficient to treat pain.

In specific embodiments, the drug delivery device is implanted at a subcutaneous site from which drug delivered from the device is released into the subcutaneous site, and then into the systemic circulation. In further specific embodiments, the formulation is delivered at a volume rate of from about 0.01 µl/day to 2 ml/day. In still other embodiments, the drug is delivered at a rate of from about 0.01 µg per hour to 2,000 µg per hour. In further embodiments, drug is delivered for a period of from about 4 weeks to 12 months. In another embodiment, the device comprises an amount of drug sufficient to provide for alleviation of pain in a subject for a period of more than 30 days. In an embodiment of particular interest, the drug is sufentanil.

One advantage of the invention is that the devices and methods described herein provide effective management of pain by administration of a relatively small quantity of fentanyl or a fentanyl congener (e.g., sufentanil), providing adequate pain relief and an improvement in adverse side effects relative to opioids, such as morphine (e.g., decreased gastrointestinal cramping). Given the adverse effects of opioid analgesics, this advantage is of considerable benefit to those requiring pain relief, particularly in relatively long term (e.g., 1–4 months) pain situations. Furthermore, the method may be more cost-effective, and thus may make pain management available to a broader population.

Another advantage of the invention is that the invention can be used to deliver relatively small quantities of fentanyl and fentanyl congeners accurately and precisely and thus safely delivering such drugs despite the extreme potency of these drugs compared to morphine. Thus, the invention allows for the convenient use of these drugs for treatment of pain ranging in severity from mild to severe.

One particular advantage of the invention is that an amount of fentanyl or a fentanyl congener sufficient to provide a relatively long duration of therapy can be stored safely and stably within the body and without deleterious effect given the high potency of the subject compounds.

Another advantage is that the drug delivery devices stores the drug formulation safely during use (e.g., without dose dumping), and release the drug formulation in a controlled fashion at a therapeutically effective rate to treat pain. Thus the devices and methods of the invention obviate undesirable bolus delivery upon implantation.

An important advantage of the invention is that the thermal expansion element accommodates thermal expansion of the formulation in the reservoir, thus minimizing the risk of initial increase of drug release due to thermal expansion of the formulation upon implantation into the body.

Another notable advantage of the invention is that the use of an implantable drug delivery device avoids the need for placement of external needles and/or catheters in the subject, which cause discomfort and can provide sites susceptible to infection. In addition, use of an implanted device increases patient compliance with a prescribed therapeutic regimen, substantially decreases or completely avoids the risk of abuse of the drug by the patient or others in contact with the patient, and affords greater mobility and easier outpatient management.

Another advantage of the invention is that fentanyl or a fentanyl congener can be delivered into the systemic circulation with such accuracy and precision and at such low quantities as to permit long-term use of such compounds to treat pain.

A further advantage is that a therapeutically effective dose of fentanyl and fentanyl congeners can be delivered at such relatively low volume rates, e.g., from about 0.01 µl/day to 2 ml/day so as to minimize tissue disturbance or trauma.

Another advantage of the invention is that substantially continuous delivery of small quantities of fentanyl or fentanyl congener (e.g., sufentanil) is effective in long-term (e.g., chronic) administration (e.g., from several weeks or from about 1 to 12 months or more).

The method of the invention is also advantageous in that since the selected drugs (e.g., sufentanil) are highly lipophilic relative to other opioids, thus facilitating delivery of the drug across the blood-brain barrier. For example, the octanol/water partition coefficient of sufentanil is 1,727, compared to a coefficient of 1.4 for morphine. Systemic administration (e.g., by subcutaneous delivery) of certain lipophilic fentanyl congeners, e.g., sufentanil, may be as effective as if the drug were delivered directly to the central nervous system.

Still another advantage is that the invention may decrease the severity or incidence of side effects normally associated with use of morphine in pain management.

Still another advantage is that the invention reduces the potential for diversion of the drug from the intended recipient, prevents the user from accidental or intentional unprescribed alteration of dose, and therefore reduces the potential for drug abuse.

These and other advantages of the invention will be readily apparent to the ordinarily skilled artisan upon reading the present specification.

Figure 1:
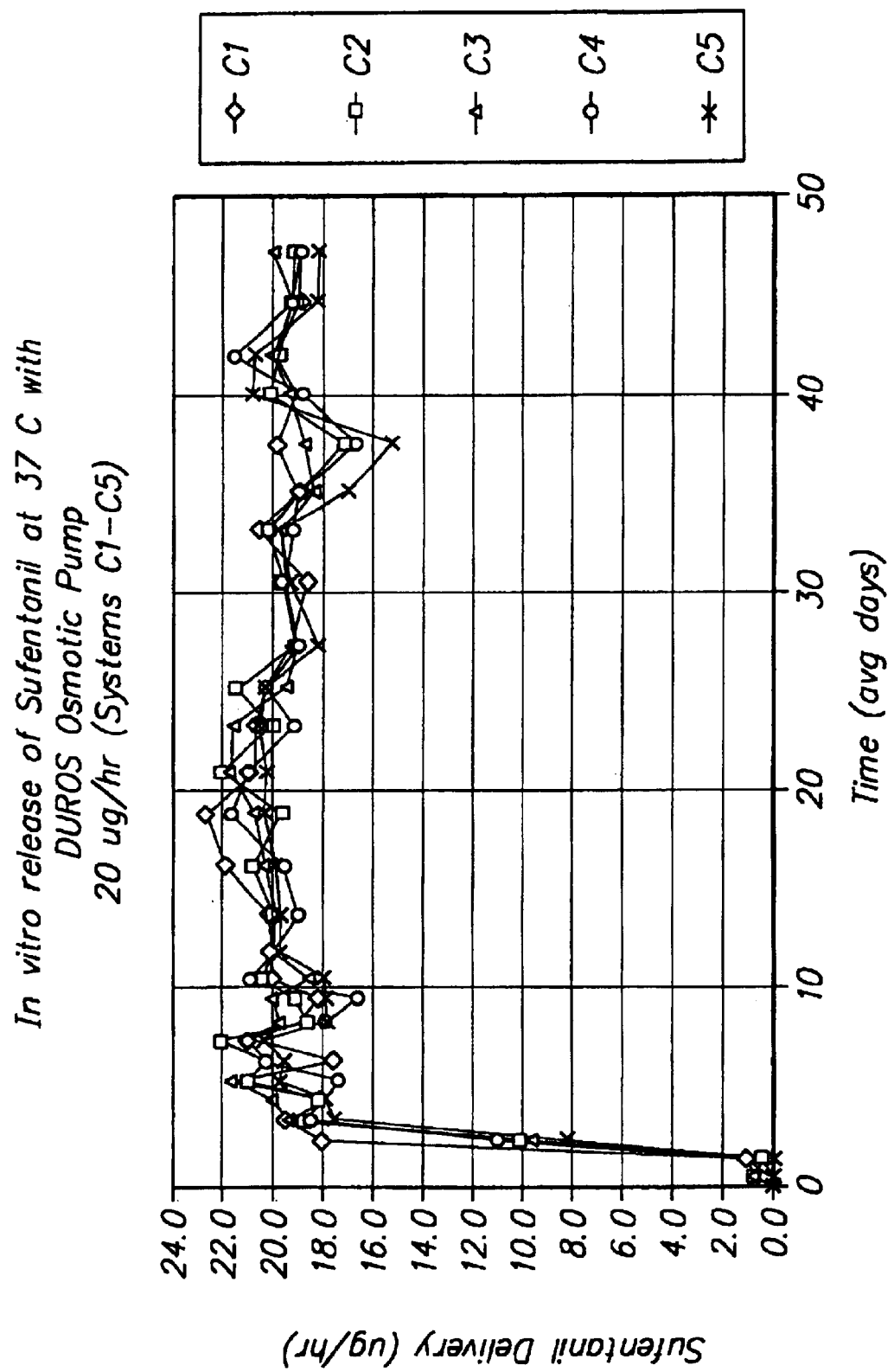
FIG. 1 is a graph showing in vitro release of sufentanil from exemplary devices comprising an osmotic pump at a rate of 20 µg/hr for a period of about 48 days.

Before the present device and methods for treatment of pain are described, it is to be understood that this invention is not limited to the specific methodology, devices, therapeutic formulations, and pain syndromes described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a drug delivery device" includes a plurality of such devices and reference to "the method of delivery" includes reference to equivalent steps and methods known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

Definitions

The term "drug" as used herein is generally meant to refer to fentanyl or a fentanyl congener (e.g., sufentanil, alfentanil, lofentanil, carfentanil, remifentanil, trefentanil, and mirfentanil), as well as formulations comprising one or more of these compounds. Use of "drug" or the phrase "fentanyl or fentanyl congener" is not meant to be limiting to use of, or formulations comprising, only one of these selected opioid compounds. Furthermore, reference to fentanyl alone or to a selected fentanyl congener alone, e.g., reference to "sufentanil," is understood to be only exemplary of the drugs suitable for delivery according to the methods of the invention, and is not meant to be limiting in any way.

The term "subject" is meant any subject, generally a mammal (e.g., human, canine, feline, equine, bovine, etc.), in which management of pain is desired.

The term "systemic delivery" is meant to encompass all parenteral routes of delivery which permit drug to enter into the systemic circulation, e.g., intravenous, intraarterial, intramuscular, subcutaneous, intra-adipose tissue, intra-lymphatic, etc.

The term "therapeutically effective amount" is meant an amount of a therapeutic agent, or a rate of delivery of a therapeutic agent (e.g., amount over time), effective to facilitate a desired therapeutic effect, such as pain relief. The precise desired therapeutic effect (e.g., the degree of pain relief, and source of the pain relieved, etc.) will vary according to the condition to be treated, the drug and/or drug formulation to be administered (e.g., the potency of the fentanyl congener, the concentration of drug in the formulation, and the like), and a variety of other factors that are appreciated by those of ordinary skill in the art. In general, the method of the invention involves the suppression or mitigation of pain in a subject suffering from pain that may be associated with any of a variety of identifiable or unidentifiable etiologies.

The term "pain management or treatment" is used here to generally describe regression, suppression, or mitigation of pain so as to make the subject more comfortable as determined by subjective criteria, objective criteria, or both. In general, pain is assessed subjectively by patient report, with the health professional taking into consideration the patient's age, cultural background, environment, and other psychological background factors known to alter a person's subjective reaction to pain.

"Delivery site" as used herein is meant to refer to an area of the body to which drug is delivered for entry into the systemic circulation, e.g., a site which allows systemic access of drug delivered to the site. Exemplary delivery sites compatible with systemic delivery of drug include, but are not necessarily limited to, subcutaneous, intravenous, intra-arterial, intra-muscular, intra-adipose tissue, and intra-lymphatic sites.

The term "implantation site" is used to refer to a site within the body of a subject at which a drug delivery device is introduced and positioned.

"Drug delivery device" as used herein is meant to any device adapted for whole implantation in a subject, and suitable for delivering the formulations for pain management according to the invention. In general, "drug delivery device" as used herein refers to an implantable device that provides for movement of drug from a reservoir (defined by a housing of the device) by action of an operatively connected pump, e.g., osmotic pumps, vapor pressure pumps, electrolytic pumps, electrochemical pumps, effervescent pumps, piezoelectric pumps, or electromechanical pump systems.

"Patterned" or "temporal" as used in the context of drug delivery is meant delivery of drug in a pattern, generally a substantially regular pattern, over a pre-selected period of time (e.g., other than a period associated with, for example a bolus injection). "Patterned" or "temporal" drug delivery is meant to encompass delivery of drug at an increasing, decreasing, substantially constant, or pulsatile, rate or range of rates (e.g., amount of drug per unit time, or volume of drug formulation for a unit time), and further encompasses delivery that is continuous or substantially continuous, or chronic.

The term "controlled drug delivery device" is meant to encompass any device wherein the release (e.g., rate, timing of release) of a drug or other desired substance contained therein is controlled by or determined by the device itself and not the environment of use. "Controlled delivery" or "controlled release" are terms used to describe delivery of drug using such a device.

"Operatively connected" as used herein means the components are provided in a device so as to function as intended. For example, a pump operatively connected to or in a housing defining a reservoir of a device of the invention is meant to indicate that, upon actuation, the pump provides for movement of formulation out of the reservoir and out of the device.

"Sustained drug delivery" refers to release or administration of drug from a source (e.g., a reservoir) over a protracted period of time. Sustained drug delivery is in effect the opposite of bolus drug delivery.

By "substantially continuous" as used in, for example, the context of "substantially continuous delivery" is meant to refer to delivery of drug (e.g., sufentanil) in a manner that is substantially uninterrupted for a pre-selected period of drug delivery (other than a period associated with, for example, a bolus injection). Furthermore, "substantially continuous" drug delivery can also encompass delivery of drug at a substantially constant, pre-selected rate or range of rates (e.g., amount of drug per unit time, or volume of drug formulation for a unit time) that is substantially uninterrupted for a pre-selected period of drug delivery.

The term "reservoir" refers to a chamber or containment space within a delivery device for storing an agent to be delivered from the delivery device.

The terms "flow path" or "flow pathway" refers to the pathway taken by an agent as it is dispensed from a reservoir of a delivery device to the outside of the delivery device.

DETAILED DESCRIPTION OF THE INVENTION

The invention relates to an implanted controlled drug delivery device, which in certain embodiments comprises a miniature pump, where the drug delivery device effects delivery of fentanyl or a fentanyl congener, e.g., sufentanil. The housing of the device defines a reservoir in a drug formulation for delivery is contained. The device further comprises a thermal expansion element, which defines a flow pathway (or orifice) having an inlet, an outlet, and a thermal expansion channel between the inlet and outlet. The thermal expansion channel compensates for initial thermal expansion of a liquid drug formulation contained in a reservoir of the device after device is implanted in the body of a subject. In various exemplary embodiments, the thermal expansion element comprises a plug, or a plug and an inner wall of the device housing. Various portions of the flow pathway of the thermal expansion element can be defined by the plug and/or the plug and an inner wall of the housing in which the plug is seated.

The device can also comprise a valve, which is positioned in the flow pathway defined by the thermal expansion element so as to prevent leakage of drug from the pump prior to use or upon implantation. This device can be implanted into a patient to provide pain relief over a protracted period of time. The device and flow pathway defined the thermal expansion element are adapted to provide for controlled release of fentanyl or fentanyl congener from the reservoir, so as to provide an accurate, sustained delivery of a drug over weeks or months. The invention thus finds particular use in delivery of fentanyl congeners, such as sufentanil, which congeners are hundreds of times to thousands of time more potent than morphine.

Pain Susceptible to Management with the Devices and Methods of the Invention

In general, administration of fentanyl or a fentanyl congener according to the invention can be used to facilitate management of pain (e.g., palliative care through, e.g., systemic or centrally mediated analgesia) that is associated with any of a wide variety of disorders, conditions, or diseases. "Pain" as used herein, unless specifically noted otherwise, is meant to encompass pain of any duration and frequency, including, but not limited to, acute pain, chronic pain, intermittent pain, and the like. Causes of pain may be identifiable or unidentifiable. Where identifiable, the origin of pain may be, for example, of malignant, non-malignant, infectious, non-infectious, or autoimmune origin. Of particular interest is the management of pain associated with disorders, diseases, or conditions that require long-term therapy, e.g., chronic and/or persistent diseases or conditions for which therapy involves treatment over a period of several days (e.g., about at least 3 days to 10 days), to several weeks (e.g., about 2 weeks or 4 weeks to 6 weeks), to several months or years, up to including the remaining lifetime of the subject. Subjects who are not presently suffering from a disease or condition, but who are susceptible to such may also benefit from prophylactic pain management using the devices and methods of the invention, e.g., prior to traumatic surgery. Pain amenable to therapy according to the invention may involve prolonged episodes of pain alternating with pain-free intervals, or substantially unremitting pain that varies in severity.

In general, pain can be nociceptive, somatogenic, neurogenic, or psychogenic. Somatogenic pain can be muscular or skeletal (i.e., osteoarthritis, lumbosacral back pain, posttraumatic, myofascial), visceral (i.e., pancreatitis, ulcer, irritable bowel), ischemic (i.e., arteriosclerosis obliterans), or related to the progression of cancer (e.g., malignant or non-malignant). Neurogenic pain can be due to posttraumatic and postoperative neuralgia, can be related to neuropathies (i.e., diabetes, toxicity, etc.), and can be related to nerve entrapment, facial neuralgia, perineal neuralgia, postamputation, thalamic, causalgia, and reflex sympathetic dystrophy.

Specific examples of conditions, diseases, disorders, and origins of pain amenable to management according to the present invention include, but are not necessarily limited to, cancer pain (e.g., metastatic or non-metastatic cancer), inflammatory disease pain, neuropathic pain, postoperative pain, iatrogenic pain (e.g., pain following invasive procedures or high dose radiation therapy, e.g., involving scar tissue formation resulting in a debilitating compromise of freedom of motion and substantial pain), complex regional pain syndromes, failed-back pain (e.g., acute or chronic back pain), soft tissue pain, joints and bone pain, central pain, injury (e.g., debilitating injuries, e.g., paraplegia, quadriplegia, etc., as well as non-debilitating injury (e.g., to back, neck, spine, joints, legs, arms, hands, feet, etc.)), arthritic pain (e.g., rheumatoid arthritis, osteoarthritis, arthritic symptoms of unknown etiology, etc.), hereditary disease (e.g., sickle cell anemia), infectious disease and resulting syndromes (e.g., Lyme disease, AIDS, etc.), headaches (e.g., migranes), causalgia, hyperesthesia, sympathetic dystrophy, phantom limb syndrome, denervation, and the like. Pain can be associated with any portion(s) of the body, e.g., the musculoskeletal system, visceral organs, skin, nervous system, etc.

Cancer pain is an example of one broad category of pain that can be alleviated according to the methods of the invention. One of the underlying causes of cancer pain is the severe local stretching of tissues by the neoplastic lesion. For example, as the cancer cells proliferate in an unrestricted manner, the tissues in the local region of cancer cell proliferation are subjected to mechanical stress required to displace tissue and accommodate the increased volume occupied by the tumor mass. When the tumor burden is confined to a small enclosed compartment, such as the marrow of a bone, the resulting pressure can result in severe pain. Another cause of cancer pain can result from the aggressive therapies used to combat the patient's cancer, e.g., radiation therapy, chemotherapy, etc. Such cancer therapies can involve localized or widespread tissue damage, resulting in pain.

Pain associated with any type of malignant or non-malignant cancer is amenable to alleviation according to the invention. Specific examples of cancers that can be associated with pain (due to the nature of the cancer itself or therapy to treat the cancer) include, but are not necessarily limited to lung cancer, bladder cancer, melanoma, bone cancer, multiple mycloma, brain cancer, non-Hodgkins lymphoma, breast cancer, oral cancers, cervical cancer, ovarian cancer, colon cancer, rectal cancer, pancreatic cancer, dysplastic nevi, endocrine cancer, prostate cancer, head and neck cancers, sarcoma, Hodgkins disease, skin cancer, kidney cancer, stomach cancer, leukemia, testicular cancer, liver cancer, uterine cancer, and aplastic anemia. Certain types of neuropathic pain can also be amenable to treatment according to the invention.

Back pain, which is also amenable to management using the methods of the invention, is another broad category of pain that can be alleviated by application of the methods of the invention. Back pain is generally due to one or more of the following six causes: (i) stress on intervertebral facet joints, caused by slippage, arthritis, wedging, or scoliosis; (ii) radiculopathy, the mechanical compression of the nerve root due to bulging discs or tumors; (iii) tendonitis or tendon sprain; (iv) muscle spasm or muscle sprain; (v) ischemia, a local insufficiency in circulatory flow; and (vi) neuropathy, damage to nervous tissue of metabolic etiology or arising from cord tumors or central nervous system disease.

The methods of the invention can be used to manage pain in patients who are opioid naive or who are no longer opioid naive, although due to the potency of the drugs administered, patients are preferably not opioid naive. Exemplary opioid naive patients are those who have not received long-term opioid therapy for pain management. Exemplary non-opioid naive patients are those who have received short-term or long-term opioid therapy and have developed tolerance, dependence, or other undesirable side effect. For example, patients who have intractable adverse side effects with oral, intravenous, or intrathecal morphine, transdermal fentanyl patches, or conventionally administered subcutaneous infusions of fentanyl, morphine or other opioid can achieve good analgesia and maintain favorable side-effects profiles with delivery of fentanyl or a fentanyl congener when administered in the dose ranges and/or low volume rates described above.

Administration of drug using an implanted device according to the invention is particularly preferred where delivery by other routes has become undesirable, e.g., the subject has experienced intractable adverse side effects with oral, intravenous, or intrathecal morphine, transdermal fentanyl patches, or conventionally administered subcutaneous infusions (e.g., using a syringe driver system or other delivery system that requires relatively high volume delivery). Delivery using an implanted device is convenient for the subject, as the implantation and removal procedures are simple and can be conducted on an out-patient basis where the patient's health allows such. Implanted drug delivery devices also increase patient compliance, prevent drug diversion and abuse, reduce the risk of infection associated with external drug delivery devices or other methods that require repeated breaking of the skin and/or maintenance of a port for administration.

Formulations of Fentanyl and Fentanyl Congeners

Fentanyl, congeners of fentanyl, and specific derivatives or analogs of fentanyl or fentanyl congeners (e.g., other derivatives, particularly 4-anilidopiperidine derivatives, of morphine) are contemplated for delivery according to the invention, although variations within the scope of the invention will be readily apparent to the ordinarily skilled artisan upon reading the disclosure provided herein. Exemplary fentanyl congeners include, but are not necessarily limited to sufentanil, alfentanil, lofenatnil, carfentanil, remifentanil, trefentanil, and mirfentanil.

The specific fentanyl congener used can vary with a variety of factors, including the therapeutic effect desired to be achieved, the patient's tolerance and/or previous exposure to opioids, etc. The relative potency of fentanyl or the fentanyl congener may also be considered in selection of the drug to be delivered. For example, the rank order of potency of fentanyl and selected fentanyl congeners relative to morphine is as follows: morphine<alfentanil< fentanyl<sufentanil<lofentanil<carfentanil. In the literature, fentanyl has been reported to be 292 times, sufentanil, 4,521 times, lofentanil 5,440 times, and carfentanil 9,441 times more potent than morphine. For a review of the pharmacokinetics of sufentanil, fentanyl, and other fentanyl congeners, see, e.g., Meert (1996) *Pharm. World Sci.* 18:1–15; Scholz et al. 1996 *Clin. Pharmacokinet.* 31:275–92.

Fentanyl or a fentanyl congener can be provided in the formulation as the opioid base and/or the opioid pharmaceutically acceptable salt, but is preferably provided in the formulation as the opioid base. The pharmaceutically acceptable salt embraces the inorganic and the organic salt. Representative salts include a member selected from the group consisting of hydrobromide, hydrochloride, mucate, citrate, succinate, n-oxide, sulfate, malonate, acetate, phosphate dibasic, phosphate monobasic, acetate trihydrate, bi(heptafluorobutyrate), maleate, bi(methylcarbamate), bi(pentafluoropropionate), mesylate, bi(pyridine-3-carboxylate), bi(trifluoroacetate), bitartrate, chlorhydrate, fumarate and sulfate pentahydrate. Where the drug formulation comprises sufentanil, use of the sufentanil base is specifically contemplated for use.

Formulations

Delivery of drug over a prolonged period of time, e.g. weeks or months, from a conveniently sized, implanted delivery system, e.g., an implantable device comprising a pump, requires a highly concentrated formulation of drug. The highly concentrated formulation of the fentanyl or fentanyl congener must be stable (e.g., at body temperatures in the case of an implanted system) and must maintain the solubility of the drug as it is delivered to the aqueous environment of the body in order to avoid precipitation and blockage of the flow pathway.

Fentanyl or a fentanyl congener can be provided in any of a variety of formulations compatible with parenteral delivery, provided that such formulation is stable (i.e., not subject to degradation to an unacceptable amount at body temperature). The concentration of fentanyl or fentanyl congener in the formulation may vary from about 0.1 wt. % to about 50 or 75 wt. %, and may be as concentrated as 95 wt. % or more. The drug can be provided in any form suitable to be carried by the controlled drug delivery device and released parenterally for systemic distribution, and is generally a flowable formulation, e.g., gel, liquid, suspension, emulsion, etc. Of particular interest is the administration of sufentanil in a form suitable for administration using an osmotic pump because of its small size.

The formulations of fentanyl and fentanyl congeners useful in the invention are characterized in that: (1) they have a fentanyl or fentanyl congener concentration of about 2, 5, 10, 500, 1,000, or 10,000 times, up to about 10,000 times or greater than that of currently commercially available formulations; (2) the fentanyl or fentanyl congener does not precipitate out when the formulation comes into contact with an aqueous environment, e.g., in the body of the subject being treated; and (3) have good stability, even at body temperatures. For example, a formulation of sufentanil in accordance with the present invention are advantageous over current commercially available sufentanil injection formulation, which contain only 50 µg/mL sufentanil as the citrate salt in aqueous solution.

In specific embodiments, the formulation comprises an amount of drug so that, when provided in a volume compatible with the size of the reservoir of the device (e.g., about 100 µl, usually less than about 150 µl) the amount of drug present in the formulation is sufficient to treat pain in the subject for a period of at least about 3 days, usually at least about 5 days, at least about 10 to 20 days, at least about 30 days, or at least about 100 days or more.

The fentanyl or fentanyl congener is generally soluble in the formulation, i.e., little or no fentanyl or fentanyl congener precipitates are present, and further, little or no fentanyl or fentanyl congener precipitates when the formulation comes in contact with an aqueous environment such as a body fluid. Precipitates of fentanyl or fentanyl congeners, when present at all, are present in the formulation at less than about 10%, less than about 7.5%, less than about 5%, less than about 2.5%, less than about 1%, or less than about 0.1% by weight of the total fentanyl or fentanyl congener present in the formulation. Whether precipitates have formed can be determined using any method known in the art, including, but not limited to, visual inspection with the unaided eye, or under low (e.g., 10× or 25×) magnification.

Formulations of the invention comprise fentanyl or a fentanyl congener in a concentration of at least about 0.5 mg/mL, 1 mg/mL, 5 mg/mL, 10 mg/mL, 25 mg/mL, 50 mg/mL, 75 mg/mL, 100 mg/mL, 150 mg/mL, 200 mg/mL, 225 mg/mL, 250 mg/mL, 300 mg/mL, 350 mg/mL, 400 mg/mL, 450 mg/mL, 500 mg/mL, or greater. Formulations of the invention comprising fentanyl or fentanyl congener are in solution, e.g., are dissolved in a liquid.

The formulations useful in the invention can comprise inactive ingredients and/or active ingredients (e.g., in addition to fentanyl or fentanyl congener).

In general, the fentanyl or fentanyl congener can be provided various formulations. Exemplary formulations are described in more detail below, as well as in PCT Publication No. WO 01/68140.

Formulations Using Cyclic Alcohols

In some embodiments, the formulation comprises fentanyl or a fentanyl congener and a low molecular weight (e.g., MW less than about 300 g/mol) alcohol, particularly a cyclic alcohol. In these embodiments, the fentanyl or fentanyl congener is present in the formulation in a concentration of from about 0.5 mg/mL to about 750 mg/mL, from about 1 mg/mL to about 450 mg/mL, from about 5 mg/mL to about 400 mg/mL, from about 50 mg/mL to about 400 mg/mL from about 75 mg/mL to about 300 mg/mL, or from about 100 mg/mL to about 250 mg/mL. Suitable low molecular weight alcohols include those which are pharmaceutically acceptable, and which preferably comprise an aromatic moiety (i.e., a cyclic alcohol), and which are relatively immiscible in water (e.g., less than about 5, less than about 4, less than about 3, less than about 2, less than about 1 gram can dissolve in 25 ml $H_2O$), including, but not limited to, benzyl alcohol, and derivatives thereof. Small amounts of other pharmaceutically acceptable substances such as other pharmaceutically acceptable alcohols, e.g., ethanol, or water, may also be present, and, if present, are present in an amount of less than about 10%, less than about 5%, or less than about 1%. In a particular embodiment, the formulation comprises fentanyl or fentanyl congener in 100% benzyl alcohol.

In other embodiments, the formulation comprises fentanyl or a fentanyl congener, a nonionic surfactant, and an alcohol ester, e.g., an ester of a low molecular weight alcohol as described above. In these embodiments, the fentanyl or fentanyl congener is present in the formulation in a concentration of from about 0.5 mg/mL to about 500 mg/mL, from about 1 mg/mL to about 450 mg/mL, from about 50 mg/mL to about 300 mg/mL, from about 75 mg/mL to about 275 mg/mL, or from about 100 mg/mL to about 250 mg/mL. Suitable alcohol esters include those which are pharmaceutically acceptable, which preferably comprise an aromatic moiety, and which are insoluble in water, including, but not limited to, benzyl benzoate, and derivatives thereof. Small amounts of pharmaceutically acceptable substances such as pharmaceutically acceptable alcohols or other pharmaceutically acceptable alcohol esters, or water, may also be present, and, if present, are present in an amount of less than about 10%, less than about 5%, or less than about 1%. In a particular embodiment, the alcohol ester is 100% benzyl benzoate.

Suitable nonionic surfactants may also be used in the formulation, including but not limited to, polysorbate, e.g., polysorbate 20, polysorbate 40, polysorbate 60; sorbitan trioleate; polyoxyethylene polyoxypropyleneglycol, e.g., polyoxyethylene(160)glycol, and polyoxypropylene(30) glycol. Other nonionic surfactants which are suitable for use in the formulations of the present invention include nonionic surfactants of the fatty acid polyhydroxy alcohol ester type such as sorbitan monolaurate, monooleate, monostearate or monopalmitate, sorbitan tristearate or trioleate, adducts of polyoxyethylene and fatty acid polyhydroxy alcohol esters such as polyoxyethylene sorbitan monolaurate, monooleate, monostearate, monopalmitate, tristearate or trioleate, polyethylene glycol fatty acid esters such as polyoxyethyl stearate, polyethylene glycol 400 stearate, polyethylene glycol 2000 stearate, in particular ethylene oxide-propylene oxide block copolymers of the Pluronics™ (Wyandotte) or Synperonic™ (ICI). In particular embodiments, the nonionic surfactant is polysorbate 20, polysorbate 40, polysorbate 60, or sorbitan trioleate, or mixtures of one or more of the foregoing.

In general, a nonionic surfactant is present in the formulation in a concentration of from about 50 mg/mL to about 200 mg/mL, from about 75 mg/mL to about 175 mg/mL, or from about 100 mg/mL to about 150 mg/mL. In a particular embodiment, the nonionic surfactant is present in the formulation at 100 mg/mL.

Delivery of Fentanyl or Fentanyl Congeners

The formulation of fentanyl or fentanyl congener is delivered from the drug delivery device at a dose that is therapeutically effective in reduction of pain (e.g., sufficient to accomplish substantial management of pain). In exemplary embodiments, the rate of delivery of sufentanil is about 3, 6, 7, 10, or 13 micrograms per hour; the rate of delivery of fentanyl is about 25, 45, 53, 75, 98 micrograms per hour. In certain embodiments, the device delivers drug at a rate of about 10 microgram per hr with the concentration of drug being about 104.4 mg/ml to 105 mg/ml. In other embodiments, the delivery rate may be about 20 microgram per hr to 25 micrograms per hr, with the concentration of drug being about 208.7 mg/ml to 209 mg/ml.

In general, administration of fentanyl or fentanyl congener according to the invention can be sustained for several days (e.g., at least about 3 days, usually at least 3 to 5 days or more), to several months or years. Typically, delivery can be continued for a period ranging from about 1 month to about 12 months or more. High-concentration formulations of fentanyl or fentanyl congener are of particular interest, and are provided by the formulations described herein.

Preferably, delivery of fentanyl or fentanyl congener is at a substantially constant, pre-selected rate or range of rates (e.g., amount of drug per unit time, or volume of drug formulation for a unit time). The drug is preferably delivered at a low volume rate of from about 0.01 µl/day to about 2 ml/day, preferably about 0.04 µl/day to about 1 ml/day, generally about 0.2 µl/day to about 0.5 ml/day, typically from about 2.0 µl/day to about 0.25 ml/day.

Delivery of drug to a subcutaneous site at a low volume rate is a particularly preferred embodiment of the invention. In one embodiment, a drug delivery device provides for substantially continuous, subcutaneous delivery of drug at a preselected rate. For example, for subcutaneous delivery of sufentanil, the drug can be delivered at a rate of from about 0.01 µg/hr to about 200 µg/hr, usually from about 0.01 µg/hr, 0.25 µg/hr, or 3 µg/hr to about 85 µg/hr, with further exemplary delivery rates being about 0.25 µg/hr, about 1 µg/hr, usually about 5 µg per hour to about 20 µg/hr, about 5 µg per hour to about 10 µg per hour, about 10 µg/hr to about 20 µg/hr, with about 5 µg/hr, about 10 µg/hr, or about 20 µg/hr being of interest, with delivery being generally up to about 200 µg/hr, and usually less than or about equal to 5 µg/hr, 10 µg/hr or 20 µg/hr. Typically delivery is between about 5 µg/hr to about 100 µg/hr. In a specific exemplary embodiment, sufentanil is delivered at a rate of from about 0.01 µg/hr, 0.1 µg/hr, 0.25 µg/hr, 1 µg/hr, and usually less than or about equal to 5 µg/hr, 10 µg/hr or 20 µg/hr, generally up to about 200 µg/hr. Appropriate amounts of fentanyl or fentanyl congener can be readily determined by the ordinarily skilled artisan based upon, for example, the relative potency of these drugs. The actual dose of drug delivered will vary with a variety of factors such as the potency and other properties of the selected drug used (e.g., lipophilicity, etc.).

For example, for subcutaneous delivery of fentanyl, the drug can be delivered at a rate of from about 0.1 µg/hr to about 2000 µg/hr, usually from about 0.1 µg/hr, 2.5 µg/hr, or 30 µg/hr to about 850 µg/hr, with further exemplary delivery rates being about 2.5 µg/hr, about 10 µg/hr, usually about 50 µg per hour to about 200 µg/hr, about 50 µg per hour to about 100 µg per hour, about 100 µg/hr to about 200 µg/hr, with delivery being generally up to about 2000 µg/hr, and usually less than or about equal to 50 µg/hr, 100 µg/hr or 200 µg/hr. Typically delivery is between about 50 µg/hr to about 1000 µg/hr. In a specific exemplary embodiment, fentanyl is delivered at a rate of from about 0.1 µg/hr, 1 µg/hr, 2.5 µg/hr, 10 µg/hr, and usually less than or about equal to 50 µg/hr, 100 µg/hr or 200 µg/hr, generally up to about 2000 µg/hr.

Drug Delivery Devices for use in the Invention

The drug delivery device of the invention is a adapted for implantation, comprises a housing which defines a reservoir in which the drug is contained, and comprises a pump that effects movement of the drug out of the reservoir and to a delivery site, after which the drug is carried via the systemic circulation to a site of action. In embodiments of particular interest comprises a miniature pump. In certain embodiments of particular interest the pump is an osmotic pump. Drug delivery devices suitable for use in the invention may be have either a fixed or adjustable delivery rate, and may be refillable.

The device further comprises a thermal expansion element, which defines a flow pathway (or orifice). The flow pathway comprises an inlet, an outlet, and a thermal expansion channel between the inlet and outlet. The thermal expansion channel compensates for thermal expansion of a liquid drug formulation contained in a reservoir of the device upon implantation into the body of the subject (i.e., as the temperature of the liquid formulation rises from storage temperature to body temperature). In various exemplary embodiments, the thermal expansion element comprises a plug, or a plug and an inner wall of the device housing. The flow pathway can be defined by the plug, the mating surfaces of the plug and an inner wall of the device housing in which the plug is seated, or both the plug and the mating surfaces of the plug and housing inner wall.

The thermal expansion channel accommodates thermal expansion of formulation within the reservoir without significantly affecting the rate of delivery by the device. The flow pathway is also of a length and dimension that facilitate controlled release for drug formulation when the device is in use. This specialized flow pathway thus provides for accurate drug delivery, and minimizes diffusion both into and out of the outlet device. The thermal expansion element is described in more detail below.

The device can further comprise a valve, which generally provides for a sealed reservoir so as to prevent leakage of drug formulation from the reservoir prior to use, keeping the reservoir safely closed until implantation. The valve is positioned within the flow pathway, and can be, for example, seated within a plug of the thermal expansion element, which in turn is positioned within the device housing. The valve is described in more detail below.

The drug delivery device can be implanted at any suitable implantation site using methods and devices well known in the art. In general, placement of the drug delivery device can be accomplished using methods and tools that are well known in the art, and performed under aseptic conditions with at least some local or general anesthesia administered to the subject. In one embodiment, the drug delivery device is implanted using an implanter such as the device provided in, for example, U.S. Design Pat. No. D402,757; or New Zealand Certificate of Registration of Design No. 29353. Removal and/or replacement of drug delivery devices can also be accomplished using tools and methods that are readily available.

In general, pumps suitable for use in the drug delivery devices of the invention are those that can deliver drug at a low dose, e.g., for sufentanil from about 0.01 µg/hr to about 200 µg/hr, and preferably at a low volume rate e.g., on the order of nanoliters to microliters per day. In one embodiment, a volume rate of from about 0.01 µl/day to about 2 ml/day is accomplished by delivery of about 80 µL/hour over a period of 24 hours, with the delivery rate over that 24 hours period fluctuating over that period by about ±5% to 10%. In certain embodiments, the pump effects delivery of drug (e.g., sufentanil) at a rate of about 10 microgram/hr with the concentration of sufentanil being about 104.4 milligram/ml. In other embodiments, the delivery rate may be about 20 microgram/hr, with the concentration of sufentanil being about 208.7 milligram/ml.

In general, the pump for use in the devices of the invention may be an osmotic pump, an electrochemical pump, an electroosmotic pump, a vapor pressure pump, an electrodiffusion pump, an electrolytic pump, an effervescent pump, a piezoelectric pump, etc. Pumps based upon a mechanical or electromechanical infusion pumps can also be suitable for use with the present invention. Examples of such devices include those described in, for example, U.S. Pat. Nos. 4,692,147; 4,360,019; 4,487,603; 4,360,019; 4,725, 852, and the like. Pumps and other convective systems are generally preferred due to their generally more consistent, controlled release over time. Convective systems in general provide for bulk movement of formulation out of the reservoir (in contrast to movement of formulation by diffusion).

Osmotic pumps are particularly preferred due to their combined advantages of more consistent controlled release and relatively small size. Of the osmotic pumps, the DUROS® osmotic pump is particularly preferred (see, e.g., WO 97/27840 and U.S. Pat. Nos. 5,985,305 and 5,728,396, all incorporated by reference, herein). In one embodiment, the controlled drug release device is an osmotic pump, with osmotic pumps of particular interest being those that effect release of formulation from the reservoir at a volume rate of from about 0.01 μl/day to about 100 μl/day (i.e., from about 0.0004 μl/hr to about 4 μl/hr), preferably from about 0.04 μl/day to about 10 μl/day, generally from about 0.2 μl/day to about 5 μl/day, typically from about 0.5 μl/day to about 1 μl/day. In one embodiment, the volume/time delivery rate is substantially constant (e.g., delivery is generally at a rate ± about 5% to 10% of the cited volume over the cited time period.

Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

The material of the housing of the delivery device is adapted for whole implantation in a subject, and as such is of a material that provides for retention of the drug formulation within the device (i.e., drug impermeable), and for exclusion of bodily fluids in the environment from the reservoir containing the drug formulation (i.e., impermeable to bodily fluids or fluids of other environment of use). The housing must also be selected so that the housing withstands pressures exerted upon the device during storage, implantation, and use. The housing thus may comprise a non-reactive polymer or a biocompatible metal or alloy. In a an embodiment of particular interest, the housing comprises a metal, e.g., stainless steel. Other metallic materials suitable for use in the reservoir of the drug release device include, titanium, platinum, tantalum, gold and their alloys; gold-plated ferrous alloys; platinum-plated titanium, stainless steel, tantalum, gold and their alloys as well as other ferrous alloys; cobalt-chromium alloys; and titanium nitride-coated stainless steel, titanium, platinum, tantalum, gold, and their alloys. The housing may comprise a metal alloy, particularly titanium or a titanium alloy having greater than 60%, often greater than 85% titanium is preferred for the most size-critical applications. Suitable polymers include, but are not necessarily limited to, acrylonitrile polymers such as acrylonitrile-butadiene-styrene polymer, and the like; halogenated polymers such as polytetrafluoroethylene, polyurethane, polychlorotrifluoroethylene, copolymer tetrafluoroethylene and hexafluoropropylene; polyethylene vinylacetate (EVA), polyimide; polysulfone; polycarbonate; polyethylene; polypropylene; polyvinylchloride-acrylic copolymer; polycarbonate-acrylonitrlle-butadiene-styrene; polystyrene; cellulosic polymers; and the like. Further exemplary polymers are described in The Handbook of Common Polymers, Scott and Roff, CRC Press, Cleveland Rubber Co., Cleveland, Ohio.

Figure 8:
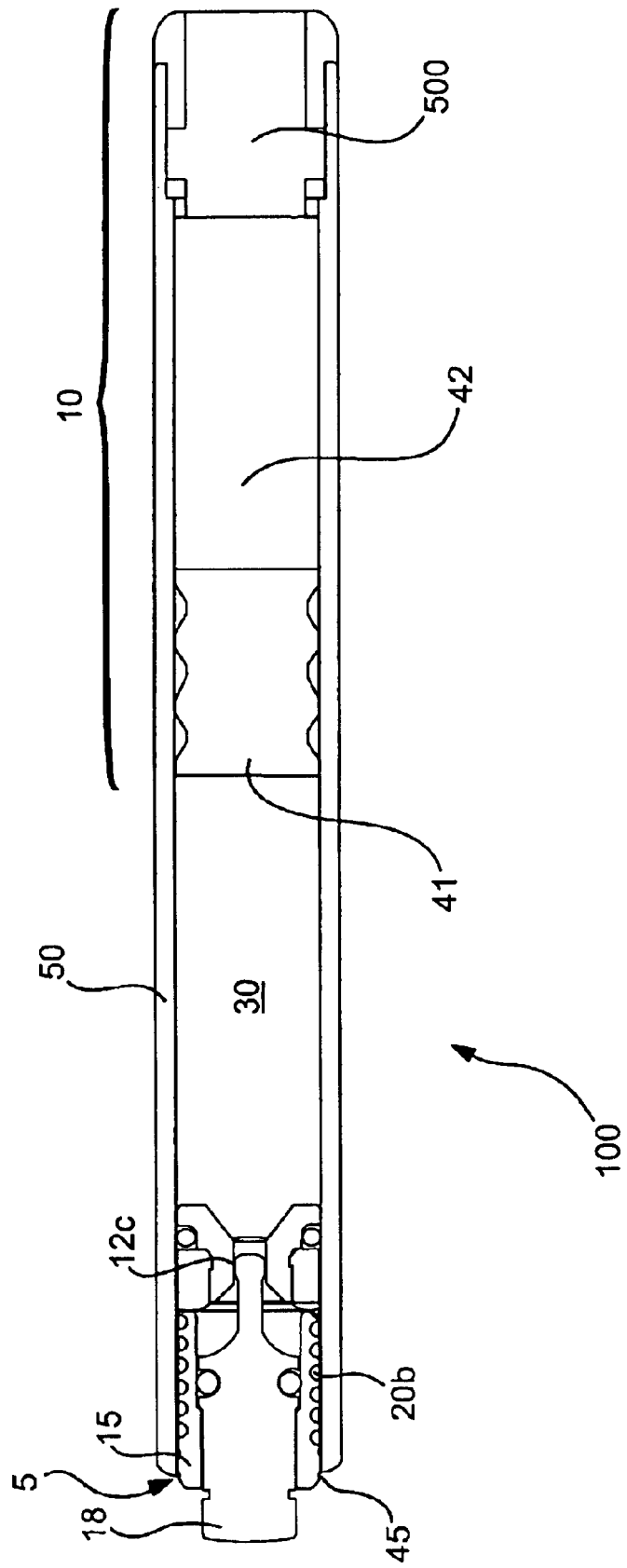
FIG. 8 is a cut-away view of drug delivery device comprising an osmotic pump containing osmotic (salt) tablets, and a sufentanil formulation. The thermal expansion element in this embodiment comprises a valve shown in the sealed position.

FIG. 8 provides an example of a system useful in the invention, and comprising an osmotic pump. The device 100 comprises a housing 50, which defines a reservoir 30. Housing 50 is adapted to contain or to be operatively connected to an osmotic pump 10, which in turn comprises a piston 41, an osmotic engine 42 and a semi-permeable, water-swellable membrane 500. Housing 50 is fitted with an exemplary thermal expansion element 5, which in this embodiment serves as both a valving and control mechanism. That is, the thermal expansion control element 5 defines a flow pathway that accommodates thermal expansion, facilitates controlled delivery, and inhibits back-diffusion and, in this embodiment, comprises a valve which keeps the flow pathway closed until use. In this embodiment, thermal expansion element 5 comprises a plug 15 and inner wall of housing 50, and defines a flow pathway a portion of which is labeled as 20b. Valve plunger 18, which is seated within plug 15 is shown in the closed position, with valve neck member 12c providing for sealing of reservoir 30. This sealed configuration is suitable preventing leakage of drug formulation during storage and shipping. In use, the device 100 is implanted, and valve plunger 18 is opened so as to provide a flow path for the formulation from reservoir 30 and out delivery outlet 45. Upon implantation, water from the environment surrounding the implanted device will move through semi-permeable membrane 500 due to the osmotic potential created by the osmotic engine 42, where the pressure so-produced will cause piston 41 to move toward reservoir 30, forcing formulation in reservoir 30 out of orifice 40.

Exemplary Thermal Expansion Elements and Valves

As noted above, the drug delivery device comprises a thermal expansion element which defines a flow pathway and, optionally, a valve, which keeps the flow pathway closed until the device is to be used (e.g., at or just prior to implantation).

The thermal expansion element, which defines a flow pathway comprising an inlet, an outlet, and a thermal expansion channel between the inlet and outlet. The thermal expansion channel compensates for thermal expansion of a liquid drug formulation contained in a reservoir of the device. In various exemplary embodiments, the thermal expansion element comprises a flow pathway that is at least partially defined by a plug, which plug can be seated within the housing. In other embodiments the thermal expansion element comprises a flow pathway that is at least partially defined by a plug seated within the device housing, and by the plug and an inner wall of the housing. Thus, the flow pathway of the thermal expansion element can be defined by the plug, the mating surfaces of the plug and an inner wall of the device housing in which the plug is seated, or both the plug and the mating surfaces of the plug and housing inner wall.

The thermal expansion element is generally positioned in the device relative to the pump so that the action of the pump effects movement of formulation from the reservoir and through the flow pathway defined by the inlet, outlet, and thermal expansion channel of the thermal expansion element. In some embodiments, the thermal expansion element is opposite the pump. In specific exemplary embodiments, the flow pathway is circuitous (e.g., helical), and extends from the formulation reservoir to a delivery outlet. The inlet of the thermal expansion element is positioned adjacent and in fluid communication with the reservoir.

The inlet and thermal expansion channel of the thermal expansion element are of a larger diameter than the end of the flow pathway defining the delivery outlet. The narrow opening of the delivery outlet facilitates regulated delivery of formulation from the reservoir without wicking of the formulation out of the reservoir, while at the same time preventing seepage of bodily fluids surrounding the drug delivery device into the drug reservoir, e.g., due to back diffusion.

The larger diameter portion of the thermal expansion element adjacent the inlet, which in turns is adjacent the formulation reservoir, serves as a thermal expansion channel. The thermal expansion control channel portion of the thermal expansion element accommodates for thermal expansion of the drug formulation within the device, which thermal expansion can occur with, for example, changes in temperature in the environment in which the device resides. Examples of such temperature changes include those that can be associated with fluctuations in storage temperatures, and with moving the device from a "shelf" environment of storage temperature (e.g., room temperature or cooler) to a body temperature environment upon implantation of the device into a human or animal patient. The thermal expansion channel of the flow pathway thus reduces the risk of or prevents deleterious burst effects (e.g., release of drug outside the acceptable range of a delivery profile).

In an embodiment of particular interest, the thermal expansion element is fitted with a valve positioned within the flow pathway, so as to provide for a closed system until the valve is actuated and the flow pathway opened prior to use. The valve for ease of transport, prevents leakage or evaporation of the reservoir contents prior to use and for the shelf life of the device, and provides for improved stability of the drug formulation prior to use (e.g., by preventing access of air or fluids to the reservoir).

Figure 5:
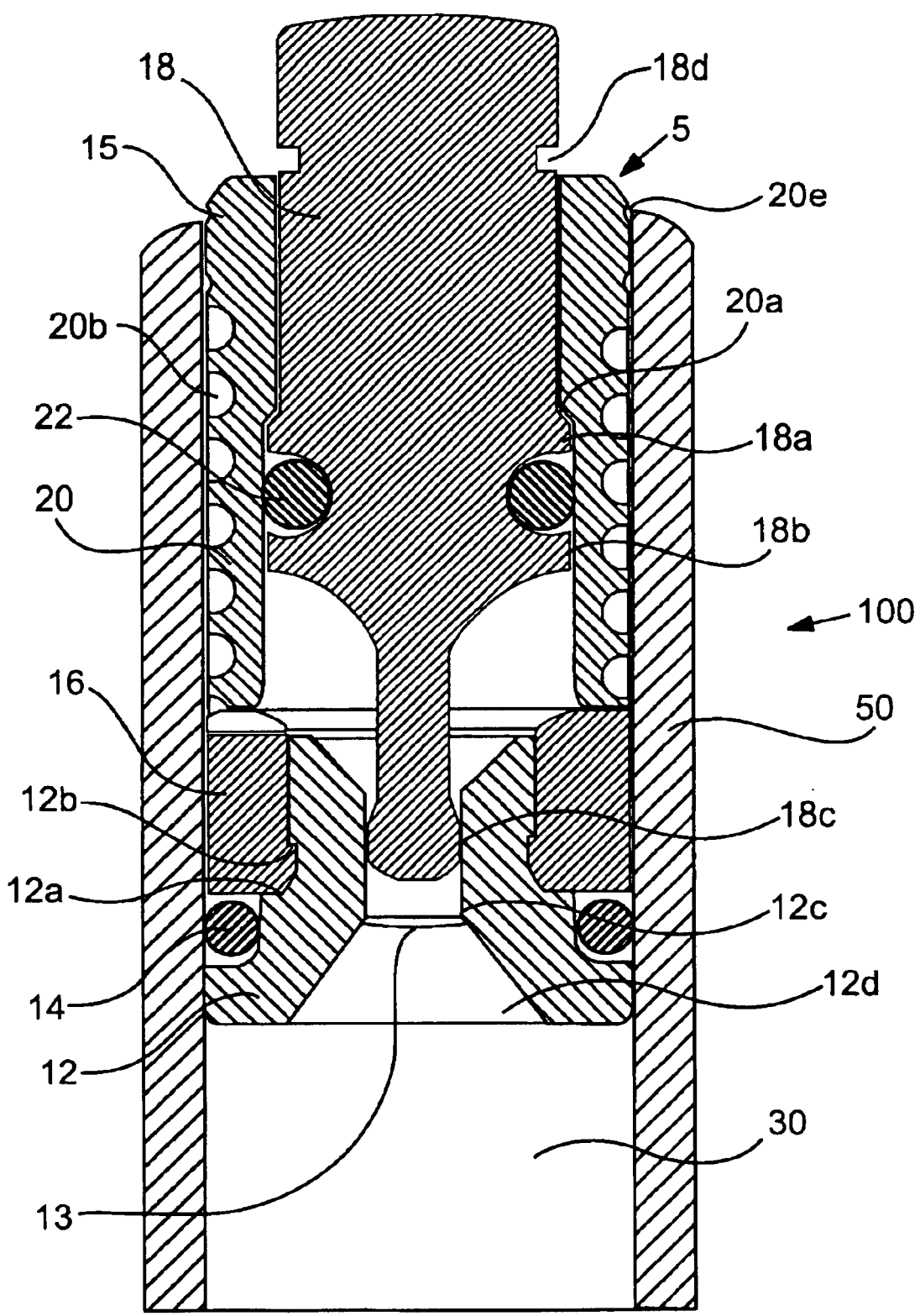
FIG. 5 illustrates a portion of a thermal expansion element comprising a valve in a position at which flow is prevented. This embodiment of the thermal expansion element both compensates for thermal expansion of the drug contained in the reservoir, and also allows the drug delivery device to be kept closed and sealed until just prior to implantation.

FIG. 5 shows an example of a thermal expansion element 5 exhibiting the above-described characteristics. Thermal expansion element 5 comprises plug 15, which comprises bottom and top ring assemblies 16, 20, and valve plunger 18, with valve 12 fitted within a housing 50, which defines reservoir 30 for holding a drug formulation to be delivered from the device 100. As described above, housing or pump body 50 may be made of titanium, for example, or other relatively rigid and biocompatible structural materials such as platinum alloys, tungsten, gold, medical grade stainless steel or other inert metals or alloys, plastics such as polyethylenes, nylons, PETS etc.

In this embodiment, thermal expansion element 5 is fixed at least partially within housing 50 to form a closed system reservoir 30 for storage of the device 100 and for controlled delivery of drug/beneficial agent upon actuation of the valve. A flow pathway defined by thermal expansion element 5 is provided adjacent reservoir 30 with an inlet of the flow pathway contacting or in fluid communication with the drug/beneficial agent contained within reservoir 30. The bottom ring assembly in this example includes a valve seat member 12 fitted within a bottom ring 16 and at least one O-ring 14 forming a seal between the valve seat member 12 and inner walls of housing 50. Valve member 12 may be formed of ultra high molecular weight polyethylene (UHMWPE), or polyethylene, or other biocompatible polymer exhibiting sufficient strength and low creep characteristics to serve as a valve seat with plunger 18 acting there against, e.g. (but not limited to): flouroelastomer (Viton™), high or low density polyethylene, linear low density polyethylene etc.

The bottom ring assembly is press fit (e.g., with about 150 lbft in this example) or otherwise securely fixed within housing 50 so that the bottom of valve seat member 12 contacts the contents of reservoir 30. As the bottom ring assembly is positioned against the reservoir 30 any air existing therebetween is drawn out by a removable vacuum line (not shown) inserted through valve neck 12c, and the valve seat member is positioned so that a meniscus 13 formed by the top of the formulation in reservoir 30 forms at the top of bottom cone 12d formed in the valve seat member 12. Bottom cone 12d in this embodiment acts to focus or funnel the formulation into the neck of valve seat member 12, thus serving as an inlet of the flow pathway defined by thermal expansion element 5.

Bottom ring 16 is locked within shoulders 12a, 12b of valve seat member 12 to provide additional stability to the placement of the valve seat member 12 and to provide integrity of the bottom ring assembly during insertion into housing 50. Bottom ring 16 may be formed of titanium, for example, or other relatively rigid and biocompatible structural materials such as platinum alloys, tungsten, gold, medical grade stainless steel or other inert metals or alloys, plastics such as polyethylenes, nylons, PETS etc. and provides a superior anchoring function due to the larger area of surface contact between bottom ring 16 and the inner walls of housing 50 (relative to the area of surface contact between valve seat member 12 and housing 50) and/or by making bottom ring 16 to have a slightly larger outside diameter than the largest outside diameter of valve member 12 so as to develop relative greater compressive forces when inserted in housing 50. Interlocking with shoulders 12a, 12b prevents movement of the valve seat member either upwardly or downwardly with respect to housing 50, thereby securely situating it in contact with the formulation in reservoir 30.

O-ring(s) 14 provide additional assurance that leakage/evaporation of drug/beneficial agent does not occur between the valve seat member 12/bottom ring assembly and the housing 50. Bottom O-ring(s) 14 may be made of VITON™ or any other biocompatible rubbers or polymers suitable for performing the sealing function indicated, e.g. (but not limited to): silicone rubber, butyl rubber, C-flex™, flouroelastomer, high or low density polyethylene, linear low density polyethylene etc.

A top ring assembly is secured in the open end of housing 50 with a bottom end of the top ring assembly abutting the top end of the bottom ring assembly to complete the thermal expansion element 5. The top ring assembly in this example includes a plunger 18, fitted within a top ring 20 and at least one O-ring 22 forming a seal therebetween. As plunger 18 is designed to slide within top ring 20, O-ring 22 may be situated between a pair of shoulders 18a, 18b to maintain O-ring 22 in the same position relative to plunger 18 as plunger 18 slides. Shoulders 18a, 18b maintain the relative position of O-ring(s) 22 while permitting O-ring(s) 22 to slide or roll along the inner walls of top ring 20, all the while maintaining the seal between plunger 18 and top ring 20.

Shoulder 18a also abuts against shoulder 20a of top ring 20 during insertion of the top ring assembly into valve/plug assembly 5. Plunger 18 and top ring 20 are dimensioned so that upon fitting into housing 50, the shoulder abutment 20a, 18a ensures that the plunger seal valving and control mechanism of plunger 18 is properly placed within the valve neck 12c of valve 12 where it seats with the valve, when the bottom end of top plug 20 abuts against the top end of bottom plug 16. The top ring assembly is securely positioned within housing 50, by press-fitting (e.g., with about 50 lbf) or by other fluid and vapor tight method of securing, such that reservoir 30 becomes a closed system for shelf storage. By press fitting the components as described, the thermal expansion element 5 can withstand back pressures (i.e, pressures provide by the drug driven by the pumping system) of up to about 5000 psi. Since most pumping systems are designed to back out at about 1000 psi, this arrangement provides more than an adequate margin of safety. The seal formed between plunger seal 18c and valve neck 12c forms a fluid and vapor tight seal, while O-ring(s) 22 provide additional assurance that no leakage/evaporation of drug/beneficial agent leaks or evaporates between plunger 18 and top ring 20 to the environment. Top ring 20 and plunger 18 may be made of titanium, for example, or other relatively rigid and biocompatible structural material such as those described previously. Top O-ring(s) 22 may be made of VITON™ or any other biocompatible materials described above for use in making O-ring 14.

A location groove 18d can be provided in plunger 18 to ensure proper placement of plunger 18 relative to top ring 20, which ultimately ensures proper positioning and sealing of the plunger seal 18c of plunger in valve neck 12c upon assembly. Since plunger 18 is slidable with regard to top ring 20, it is possible that plunger 18 could be inadvertently depressed, or slid downwardly, at least partially relative to top ring 20 during assembly. This could possibly result in distending plunger seal 18c below valve neck 12c so that a proper seal for shelf storage would not be formed. Location groove 18d is formed at a location along plunger 18 which ensures that, as long as location groove 18d is visible, it is assured that the plunger 18 is located with shoulder 18a abutted against shoulder 20a, or plunger 18 is at least high enough relative to top ring 20 so that plunger seal 18c will seat with valve seat 12 in the valve neck 12c.

By assembling both bottom and top ring portions as described above, the valve 12 of thermal expansion element 5 in this embodiment converts reservoir 30 to a closed system reservoir, thereby sealing the contents of reservoir 30 (drug/beneficial agent) for shelf storage of device 100 and preventing leakage or evaporation of the drug/beneficial agent from device 100 during storage and as long as valve 12 of thermal expansion element 5 is maintained in the configuration shown in FIG. 5.

Figure 6:
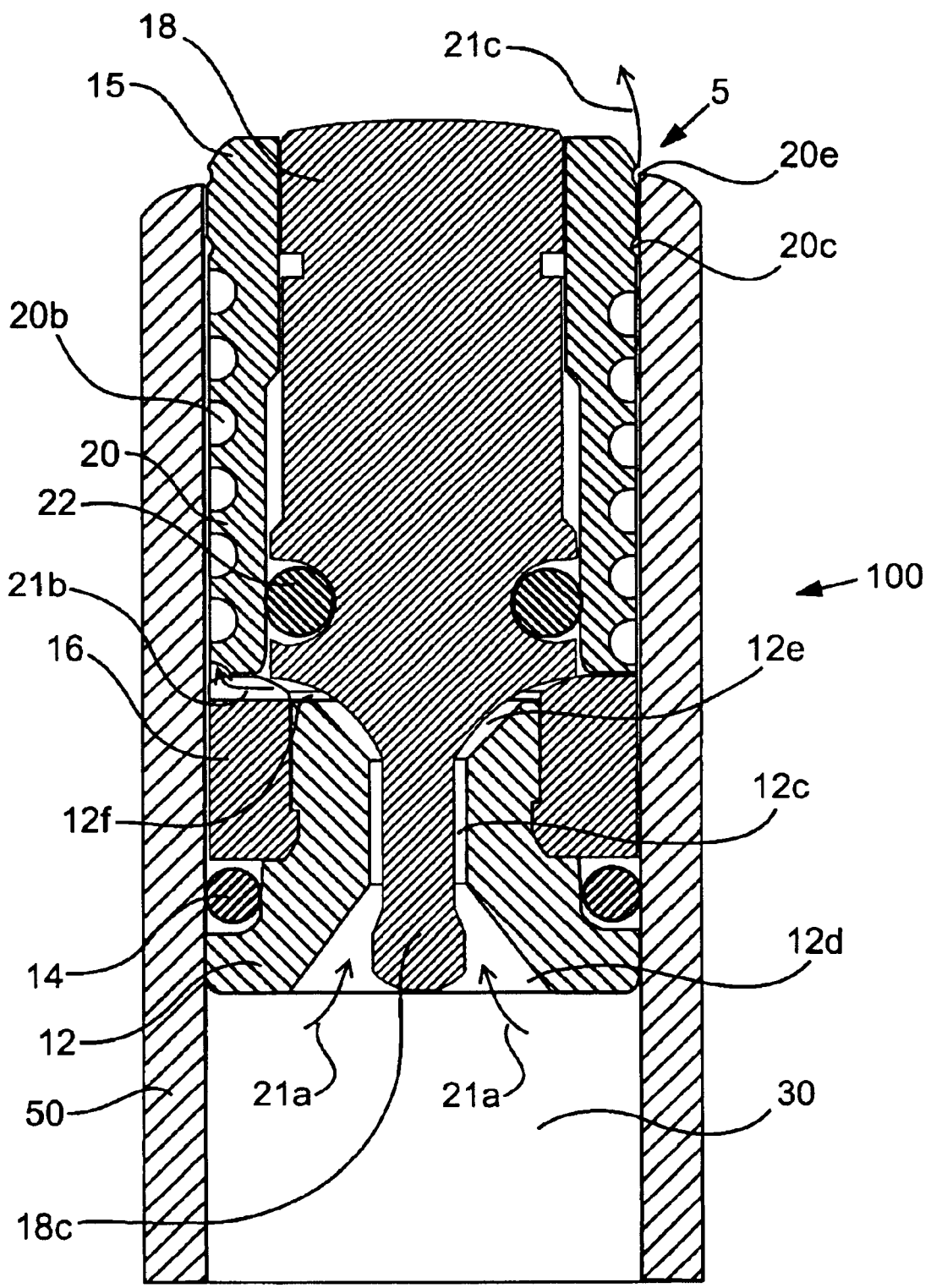
FIG. 6 illustrates the delivery device as in FIG. 5, but with the valve of the thermal expansion element positioned to allow flow from the delivery device.

When it comes time to implant device 100 or otherwise place it in an environment of use, valve 12 is actuated by depressing on plunger 18 as shown in FIG. 6, thereby opening reservoir 30 to the flow path that leads out of device 100 for delivery of drug/beneficial agent to the environment of use. In the example of FIGS. 5 and 6, plunger 18 is depressed relative to housing 50 to a position where the top of plunger 18 is substantially flush with the top end of top ring 20. Actuation/depression of plunger 18 requires about 3–4 lbf, for example, and once depressed, top O-ring 22 maintains the plunger in the depressed position against forces of up to about 0.5 lbf. This actuation forces plunger seal 18c out of valve neck 12c and into the volume defined by bottom cone 12d, thereby breaking the seal formed between plunger seal 18c and the valve seat (i.e., valve neck 12c) thereby opening the flow pathway to the inlet adjacent the formulation reservoir through valve seat member 12 between valve neck 12c and plunger 18. This flow path further connects with a space defined between the plunger 18 and top cone 12e formed in valve seat member, which in turn flows into channel 12f that connects with flow path 20b formed in top ring 20 and bordered by the inner walls of housing 50. The complete flow pathway from reservoir 30 and delivery outlet 20e is as follows: along arrows 21a from bottom cone 12d to top cone 12e, through channel 12f along arrow 21b, through channel 20b defined by a wall of housing 60 and a wall of plug 15, which channel narrows to channel 20c prior to exit through delivery outlet 20e along arrow 21c. The flow pathway thus defined forms a widely patent or open delivery channel (or orifice) which allows the uniform flow of drug/beneficial agent from the reservoir 30 to the environment of use during the operation of the pumping system as it provides a driving force to the reservoir 30.

When describing the exit channel as "widely patent" it is meant that the flow pathway is clearly open and unobstructed with a size sufficient to allow clear, even and unobstructed flow of a fluid therethrough. As noted above, in a preferred embodiment, the flow pathway (or orifice) varies in diameter along its length such that the widest portion is adjacent the formulation reservoir, and the narrowest portion defines a delivery outlet. Thus, if the flow pathway were "unwound" so as to be linear rather than helical, the flow pathway would appear in some embodiments as a conical shape, which narrows from the inlet end to the delivery outlet end. The wider portion of the flow pathway, which includes the thermal expansion channel, accommodate thermal expansion of the formulation. The narrowed portion of the orifice, including the outlet is adapted to prevent or diminish back-diffusion of fluids and molecules from the environment of use, and further minimizes diffusion as a driving force of drug delivery, so that convection is the primary force responsible for drug delivery.

In the example shown, the flow pathway is formed as a spiral or helical pathway, which provides a relatively larger volume capacity than that of a straight flow pathway, given the same cross-sectional dimensions of the pathways. The flow pathways described above (including top ring flow path 20b and the pathways connecting it to the drug/beneficial agent) provide a thermal expansion space or capacity for the drug/beneficial agent to flow into after actuation of the valve of the thermal expansion element (FIG. 6) to prevent a burst effect upon implantation of device 100 into a subject or other environment of use having a significantly higher temperature that would cause the volume of the drug/beneficial agent to expand and thus drive an amount of drug/beneficial agent from the reservoir prior to any pumping action by the pumping mechanism.

For example, a drug formulation in a device as shown might expand by about 2 microliters in a device 100 with a titanium housing after stabilization of the temperature of the device after having been moved from, for example, refrigeration to room temperature, from room temperature to a human body environment. In such a case, the thermal expansion channel of the thermal expansion element would be designed to have a volume of about 3 microliters so as to have an extra margin of safety to ensure that a burst of drug would not be initially delivered to the patient upon implantation. Of course, the volumes described are only an example, and the actual volume of the thermal expansion channel for preventing the burst effect will vary depending upon the total volume of the drug in the reservoir, the cross sectional area(s) of the thermal expansion channel, the change in temperature from the first to the second environment, etc. Generally, however, the volume of the thermal expansion channel will be designed such that, upon thermal expansion of the drug/beneficial agent in the environment of use, the drug/beneficial agent will extend no more than about two thirds of the way along the length of the top ring flow path 20b.

Further exemplary thermal expansion elements and valves that may be used in the invention are described in PCT application serial no. PCT/US01/43143, filed Nov. 21, 2001 and in U.S. provisional application Ser. No. 60/323,406, fled Sep. 17, 2001, respectively.

Implementation of the Devices and Methods of the Invention in Subjects

In use, the drug delivery device and dosage are selected according to the needs of the subject, and the device implanted into the subject.

Selection of an appropriate dose of fentanyl or fentanyl congener for a patient is important for both safety and efficacy. Identification of the appropriate dose of fentanyl or fentanyl congener is particularly important where the implanted drug delivery device delivers drug at a fixed delivery rate that cannot be altered after implantation. Drug delivery devices can be selected or adjusted so as to provide for administration of a desired dosage, e.g., by adjusting the volumetric rate of delivery from the device or the concentration of the formulation delivered from the device. For example, where the device comprises an osmotic pump (for example as shown in FIG. 8), a desired volumetric delivery rate from the osmotic pump can be achieved by selection of a semi-permeable membrane with the appropriate permeability to water which influences the rate at which water is imbibed into the osmotic chamber, which in turn affects the rate at which the piston of the pump moves and displaces formulation). Additionally, in the exemplary osmotic pump shown in FIG. 8, an specific dosage of the drug delivered from the device can achieved by selection of a formulation with the appropriate concentration of fentanyl or fentanyl congener.

In general, the appropriate dosage of fentanyl or fentanyl congener to be delivered to a patient in accordance with this invention can be determined by a variety of means. See Example 1 (Selection of Appropriate Dose).

Once a device and therapeutic regimen (e.g., formulation concentration, delivery rate, duration of delivery, and the like) is selected, the device capable of delivery of fentanyl or fentanyl congener in accordance with the selected regimen is then implanted at an implantation site in the subject. Implantations sites include, but are not necessarily limited to, any suitable soft tissue site that is compatible with systemic delivery of drug. In general, the implantation site is any suitable site under the skin of the subject (e.g., subcutaneous, subdermal) or an intramuscular site. Subcutaneous implantation sites are preferred because of convenience of implantation and removal of the drug delivery device.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

Treatment Regimen for Subcutaneous Delivery of Fentanyl or Fentanyl Congener

The following is an exemplary treatment regimen. The approximate volume rate of release may be about 1.5 microliters per hour, with approximately zero order kinetics, for over 3 days.

1. Evaluation of Patient

The physician first examines the potential patient and evaluates the patient's history to determine if the patient has pain that amenable to treatment by fentanyl and congeners and can safely tolerate such treatment.

2. Selection of Appropriate Dose

If the physician decides to proceed with treatment in accordance with this invention, the physician determines the appropriate dose of drug (e.g., sufentanil or fentanyl) to be administered to the patient. This determination can be performed in a variety of ways.

If the patient is already using medication to control pain (e.g., oral morphine or the fentanyl transdermal patch), the physician can correlate the dose of medication previously used by the patient to an appropriate dose of the selected drug (e.g., fentanyl or fentanyl congener such as sufentanil) when infused subcutaneously. This correlation can be made by reference to dose conversion information (e.g., a dose conversion chart) between the previous medication and the selected drug, if such dose conversion information exists.

If dose conversion information does not exist for the previous medications and the selected drug, the physician can first switch the patient from the previous medications to another medication for which there exists dose conversion information with the selected drug (e.g., fentanyl or fentanyl congener, e.g., sufentanil).

In the alternative to resorting to dose conversion information, or if such information does not exist, the physician can determine the appropriate dose of drug to treat such patient by infusing the selected drug (e.g., fentanyl or fentanyl congener, e.g., sufentanil) subcutaneously by means of an external pump and adjusting such infusion rates until the proper dose to control the pain with minimal side effects is located.

Alternatively, the physician can transition the patient from his or her previous pain medication (e.g., oral morphine) to transdermal fentanyl, e.g., using the Duragesic® patch (transdermal fentanyl, Janssen) according to usual clinical practice (e.g., over a six-to-nine day period). Once the patient's dose for transdermal fentanyl is stable and comprises at least about 70% or more of daily opioid consumption, the patient's fentanyl dose is converted to a sufentanil dose based on a 1:7.5 potency ratio. This information allows selection of an appropriate drug dose from the implanted device.

An appropriate device adapted for implantation and for delivery of the appropriate drug delivery rate is selected and implanted in the patient. Treatment using the fentanyl transdermal patch (or other prior therapy) can be continued until drug delivery is initiated from the implanted device or can be continued as concomitant or "break-through" medication.

3. Implantation of a Drug Delivery Device

Once the physician has determined the appropriate dose of fentanyl or fentanyl congener (e.g., sufentanil), then the physician selects a drug delivery device containing a formulation comprising the selected drug (e.g., sufentanil) that is capable of delivering the required dosage for up the selected treatment period (e.g. 3 months). The physician will then implant the drug delivery device into the subcutaneous tissue at the inside of the upper arm of the patient.

4. Treatment of Pain

Once the drug delivery device containing the fentanyl or fentanyl congener (e.g., sufentanil) formulation has become activated by implantation, the drug will be delivered systemically to control pain for the selected treatment period (e.g. 3 months). Treatment can be stopped prior to the end of such 3 months by explanting the drug delivery device. If treatment is desired to be extended past the initial treatment period, the expended device can be explanted and a replacement device may be implanted in the same subcutaneous location.

Example 2

Drug Loading for Device Comprising an Osmotic Pump

Figure 7:
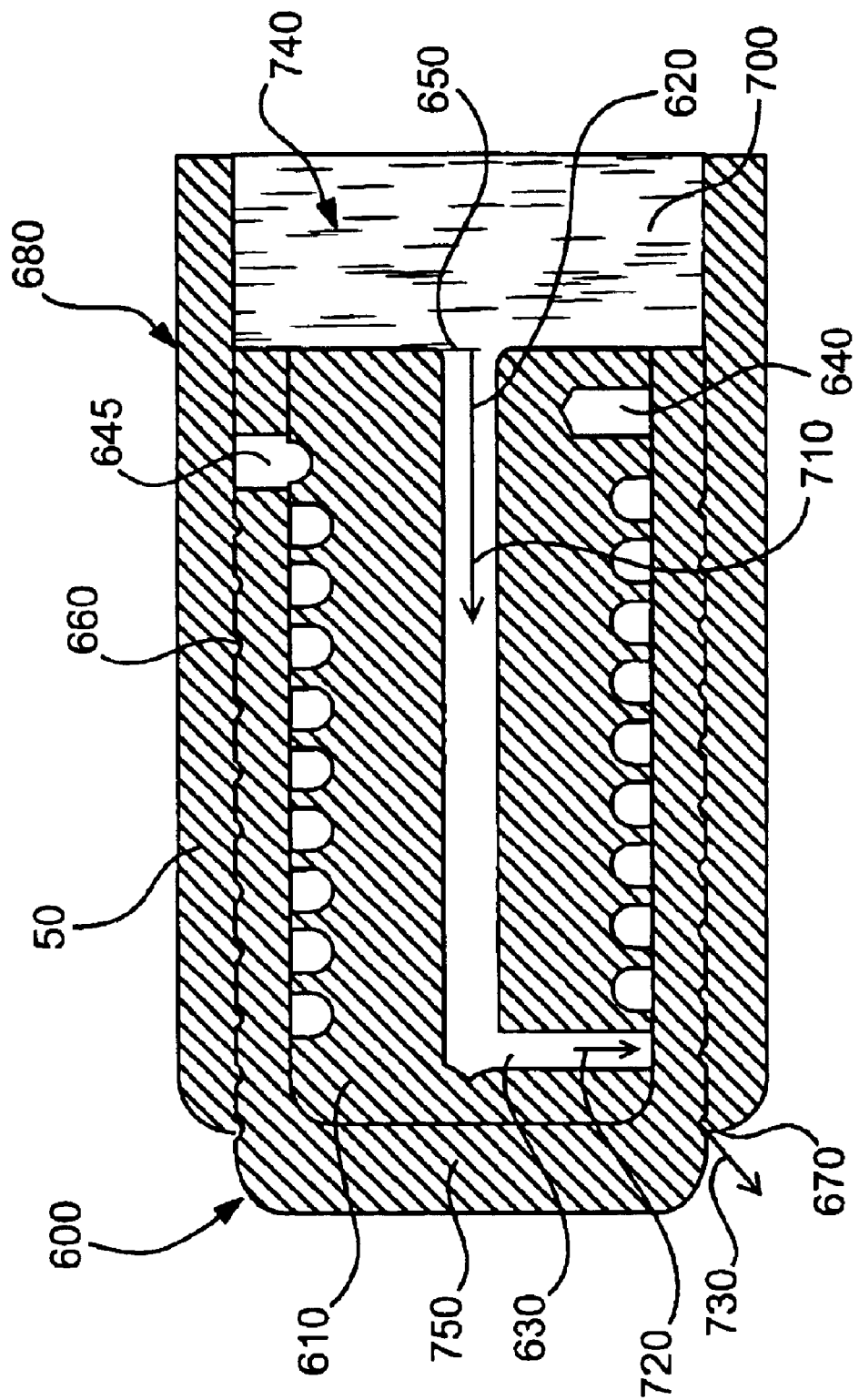
FIG. 7 is a cut-away view of a thermal expansion element positioned for use in the housing of a drug delivery device.

The following is a description of exemplary drug loading parameters of a device comprising an osmotic pump used for the delivery of sufentanil. In this example, the thermal expansion element of the device comprised a plug as illustrated in FIG. 7, which plug defines an inlet, an expansion control channel and an outlet. At least a portion of the delivery outlet is defined by the plug and an inner wall of housing 50. As shown in FIG. 7, plug 600 is inserted in housing 50 and is in fluid communication with formulation 740 contained in reservoir 700 of drug delivery device 680. Plug 600 comprises inner plug member 610 positioned within outer plug member 750. Expansion control channel 620 extends longitudinally from a first end of inner plug member 610 (which end defines inlet 650) and through the body of the inner plug member; a laterally extending section, which extends from the body of the inner plug member 610 and to an outer wall of the inner plug member 610, and a helical portion, defined by the mating surfaces of inner plug member 610 and outer plug member 750. Exit channel 660, which is defined by the mating surfaces of an outer wall of outer plug member 750 and an inner wall of housing 50, communicates with expansion control channel 620 via passage 645 through a wall of outer plug member 750. Timing hole 640, represented by a dead-end passage at the end of inner plug member 610 adjacent reservoir 700 during use, facilitates manufacture and assembly of the plug to ensure that expansion control channel 620 and exit channel 660 are in fluid communication. In use, formulation 740 flows from reservoir 700 into inlet 650, through expansion channel 620 along arrow 710 through gate 645 and into exit channel 660, and out outlet 670 at arrow 730. The plug was machined from titanium, and press-fit onto the housing.

The parameters are based on a nominal fill volume of the device reservoir of 155 $\mu l$, with a nominal volumetric delivery rate of 1.4 $\mu l$/day for a nominal duration of 110 days (to ensure that a target delivery period of 90 days is achieved). An exemplary device used in this protocol is approximately 3.76 mm in diameter and 44.21 mm in length.

drug was dissolved in the benzyl alcohol by stirring with a magnetic stirrer. When the resultant preparation was clear, additional benzyl alcohol was added to obtain 10 mL of formulation. The resultant formulation concentration was 310 mg/mL.

208 mg/mL formulation: 2.08 g of sufentanil base were weighed out and added to a portion of benzyl alcohol. The drug was dissolved in the benzyl alcohol by stirring with a magnetic stirrer. When the resultant preparation was clear, additional benzyl alcohol was added to obtain 10 mL of formulation. The resultant formulation concentration was 310 mg/mL.

104 mg/mL formulation: 1.04 g of sufentanil base were weighed out and added to a portion of benzyl alcohol. The drug was dissolved in the benzyl alcohol by stirring with a magnetic stirrer. When the resultant preparation was clear, additional benzyl alcohol was added to obtain 10 mL of formulation. The resultant formulation concentration was 310 mg/mL.

Example 4

Release of Sufentanil from a Device Having an Osmotic Pump, In Vitro

The release of drug from a device comprising an osmotic pump as in Example 2 at 37° C. was tested in vitro at either 20 $\mu g$/hr or 5 $\mu g$/hr drug dose rates. Five different systems (five different devices comprising pumps) were tested for each of the drug delivery rates (20 $\mu g$/hr and 5 $\mu g$/hr) over a 48 day period.

The release media (RM) is prepared from a phosphate buffered saline (PBS) solution, available commercially as a powder preparation and prepared according to manufactur-

TABLE 1

Loading Parameters

| Dose rate $\mu g$/hr | Dose rate $\mu g$/day | $\mu g$ delivered over 110 days | mg delivered over 110 days | Nominal Rate $\mu l$/day | Nominal Rate $\mu l$/hr | Device Residence Volume | wt/vol % formulation load |
|---|---|---|---|---|---|---|---|
| 2.5 | 60 | 6600 | 6.6 | 1.4 | 0.058 | 155 | 4.28 |
| 5 | 120 | 10800 | 10.8 | 1.4 | 0.058 | 155 | 8.57 |
| 7.5 | 180 | 16200 | 16.2 | 1.4 | 0.058 | 155 | 12.6 |
| 10 | 240 | 21600 | 21.6 | 1.4 | 0.058 | 155 | 17.1 |
| 20 | 460 | 43200 | 43.2 | 1.4 | 0.058 | 155 | 34.3 |

These parameters thus dictate the amount of drug to be included in the formulation in order to provide for delivery at the selected dose rate for an approximately 110 day period (e.g., about 3 months).

Example 3

Formulations Comprising Sufentanil in Benzyl Alcohol 397 mg/mL formulation: 3.97 g of sufentanil base were weighed out and added to a portion of benzyl alcohol. The drug was dissolved in the benzyl alcohol by stirring with a magnetic stirrer. When the resultant preparation was clear, additional benzyl alcohol was added to obtain 10 mL of formulation. The resultant formulation concentration was 397 mg/mL.

310 mg/mL formulation: 3.10 g of sufentanil base were weighed out and added to a portion of benzyl alcohol. The er's directions. 5% polysorbate 20 was added to the media prior to bringing it to final volume. This solution is the release media (RM). 6 mL of RM was dispensed into a 15 mL conical polypropylene tube, with one tube prepared for each system to be tested. The tubes were placed in a 37° C. water bath and allowed to reach temperature.

A system containing sufentanil is placed into each tube with orifice end down, and completely immersed in the RM. At desired time intervals, the system is removed from the tube using a transfer rod. The system is placed (orifice end down) into a new tube of RM which has been equilibrated in the water bath. An example of time intervals is 0.5 hours, 1, 2, 3, 4, 5, 6, 7, 14, 28, 35 days, continuing weekly until delivery is complete.

In order to determine the amount of sufentanil released, 4 mL of acetonitrile was added to each sample test tube and mixed thoroughly. The sample is then assayed to determine the amount of sufentanil released during the time interval. Sufentanil in the samples was quantitated by HPLC or other methodology capable of quantitating sufentanil in the presence of formulation and RM. The amount released per unit time was calculated for each interval, and a release rate profile prepared by plotting the amount released per unit time on the y-axis against the mean time interval on the x-axis.

Figure 2:
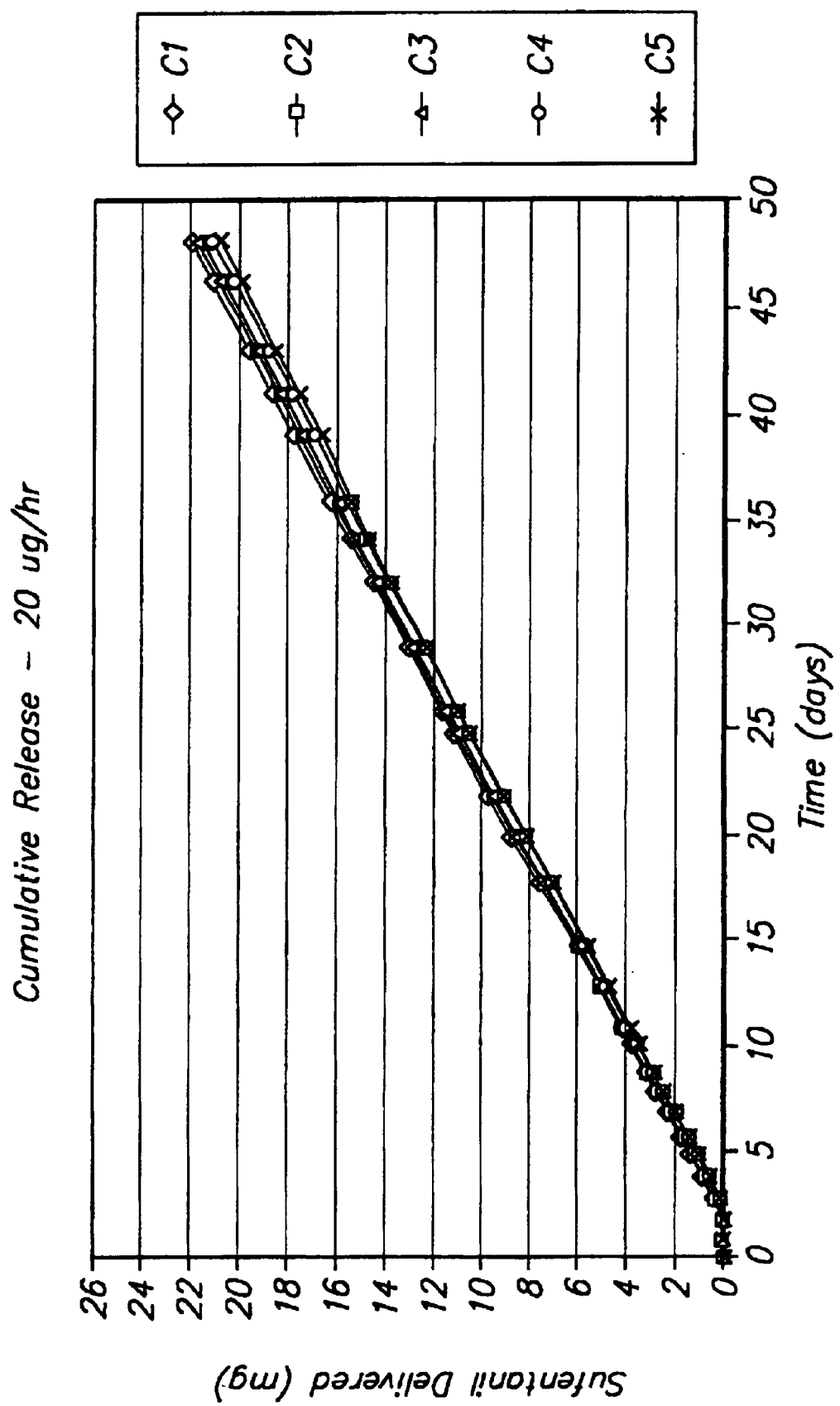
FIG. 2 is a graph showing cumulative in vitro release of sufentanil from exemplary devices comprising an osmotic pump at a rate of 20 µg/hr for a period of about 48 days.
Figure 3:
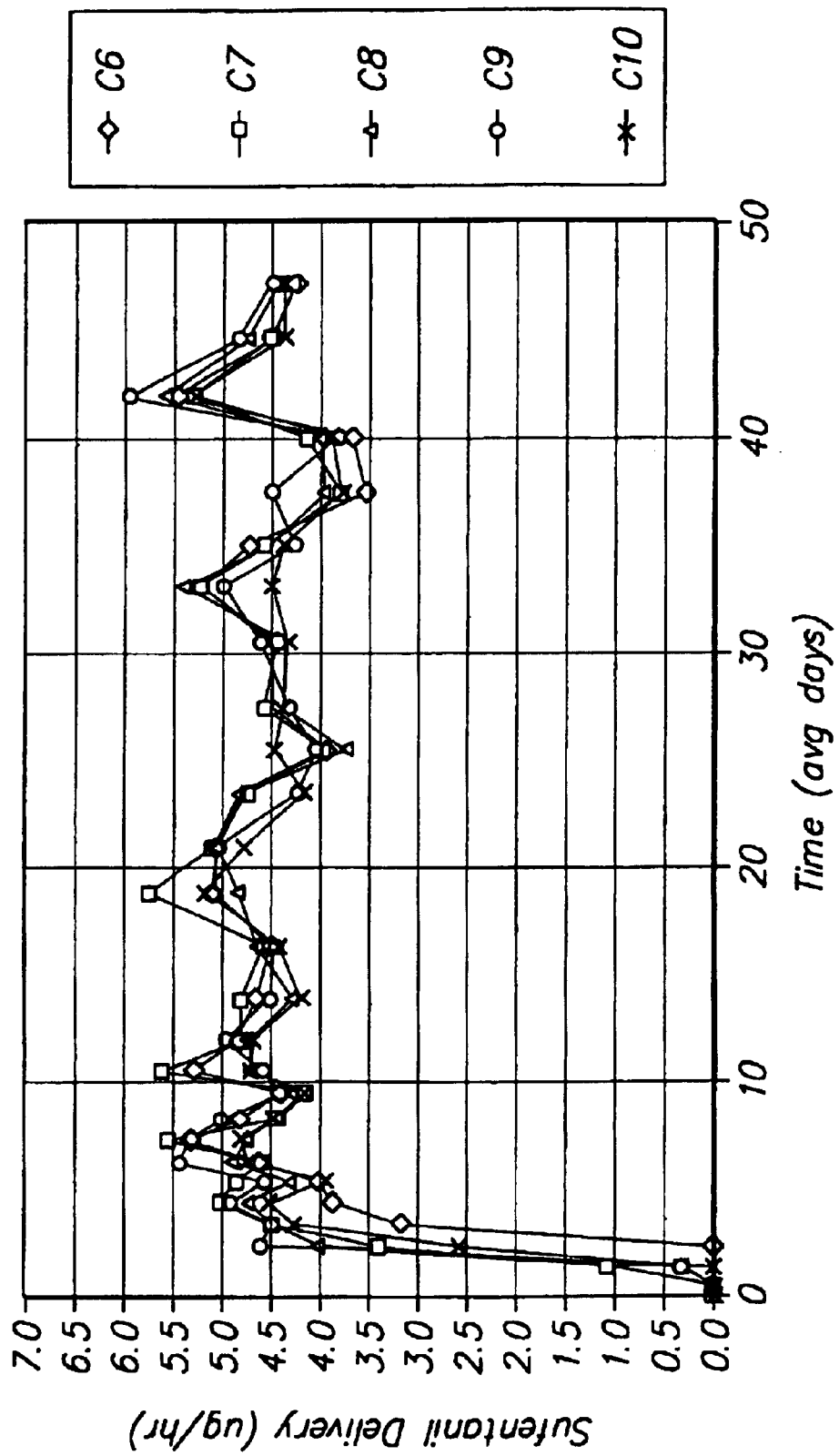
FIG. 3 is a graph showing in vitro release of sufentanil from exemplary devices comprising an osmotic pump at a rate of about 5 µg/hr for a period of about 48 days.
Figure 4:
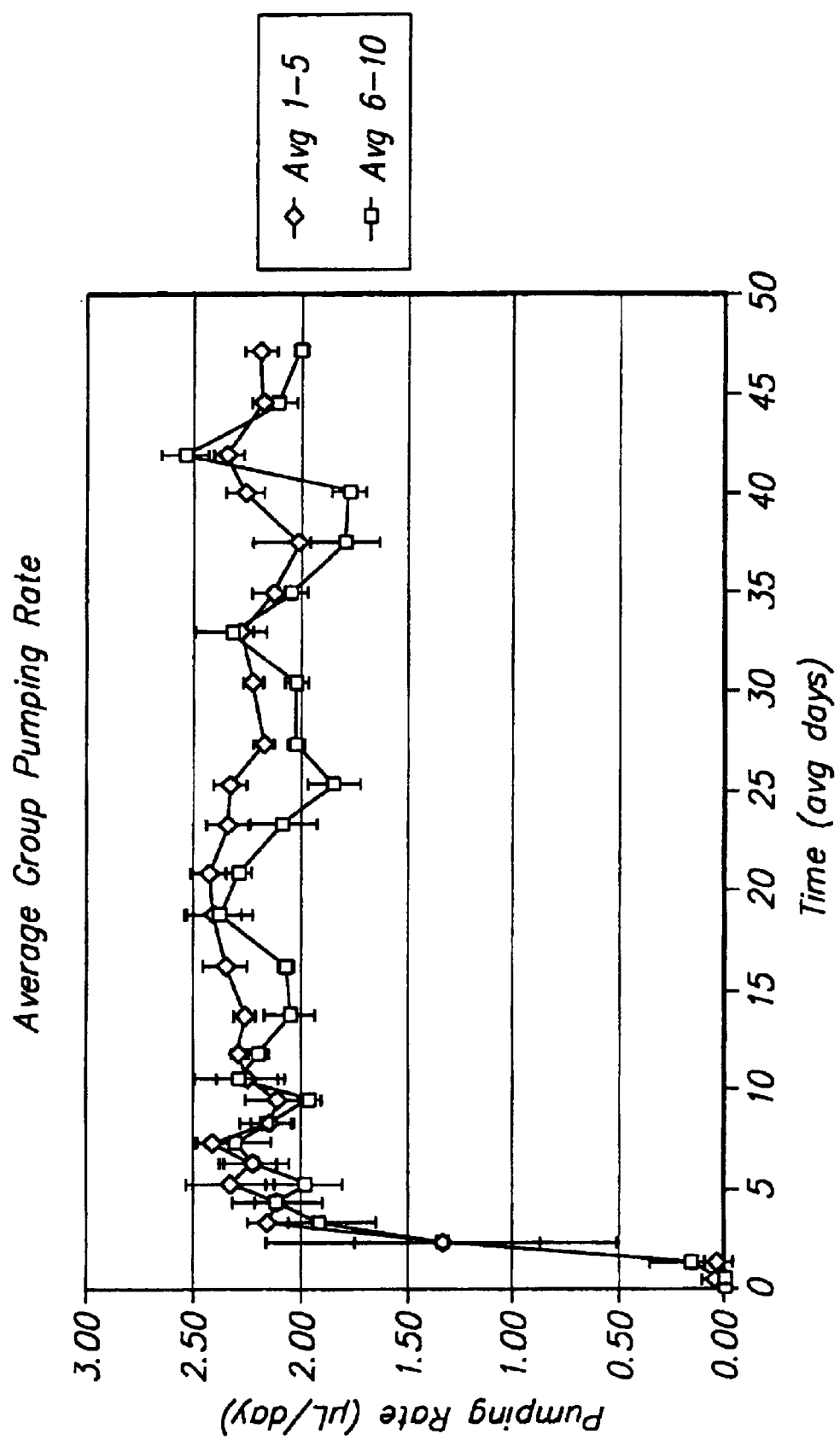
FIG. 4 is a graph showing the average pumping rates (microliters per day) of the devices of FIGS. 1 and 3, with an average pumping rate being between about 2 and 2.5 microliters per day.

The results for the 20 μg/hr system are provided in FIG. 1, with the cumulative release provided in FIG. 2. The results for the 5 μg/hr system are provided in FIG. 3. The average pumping rate for each group (the 20 μg/hr group of devices and the 5 μg/hr group of devices) is provided in FIG. 4. The results demonstrate that controlled, continuous, and precise low volume release of the potent opioid sufentanil is achieved with an implanted device comprising a pump. In vitro release by the device is correlated to in vivo release because the volume dispensed from the device is a pure function of the pump and is independent of the environment surrounding the pump. Thus, these same devices are expected to perform the same in vivo as in vitro.

Example 5

In Vitro Release of Sufentanil from a Device Comprising an Osmotic Pump

In this example a device having an osmotic pump as shown in FIG. 8, having a thermal expansion element and valve assembly as in FIGS. 5 and 6.

The housing into which the plug is to be inserted is approximately 3.150 mm in diameter, and approximately 43.18 mm in length. The components were press fit together. The reservoir of the drug delivery device was filled with approximately 155 μl of sufentanil formulation, formulated with benzyl alcohol to a concentration of about 179.58 mg/ml. The device was tested by placing the device with the plug in place in a 37° C. water bath filled with PBS to simulate implantation in the body, and measuring the rate of drug delivery from the device.

Figure 9:
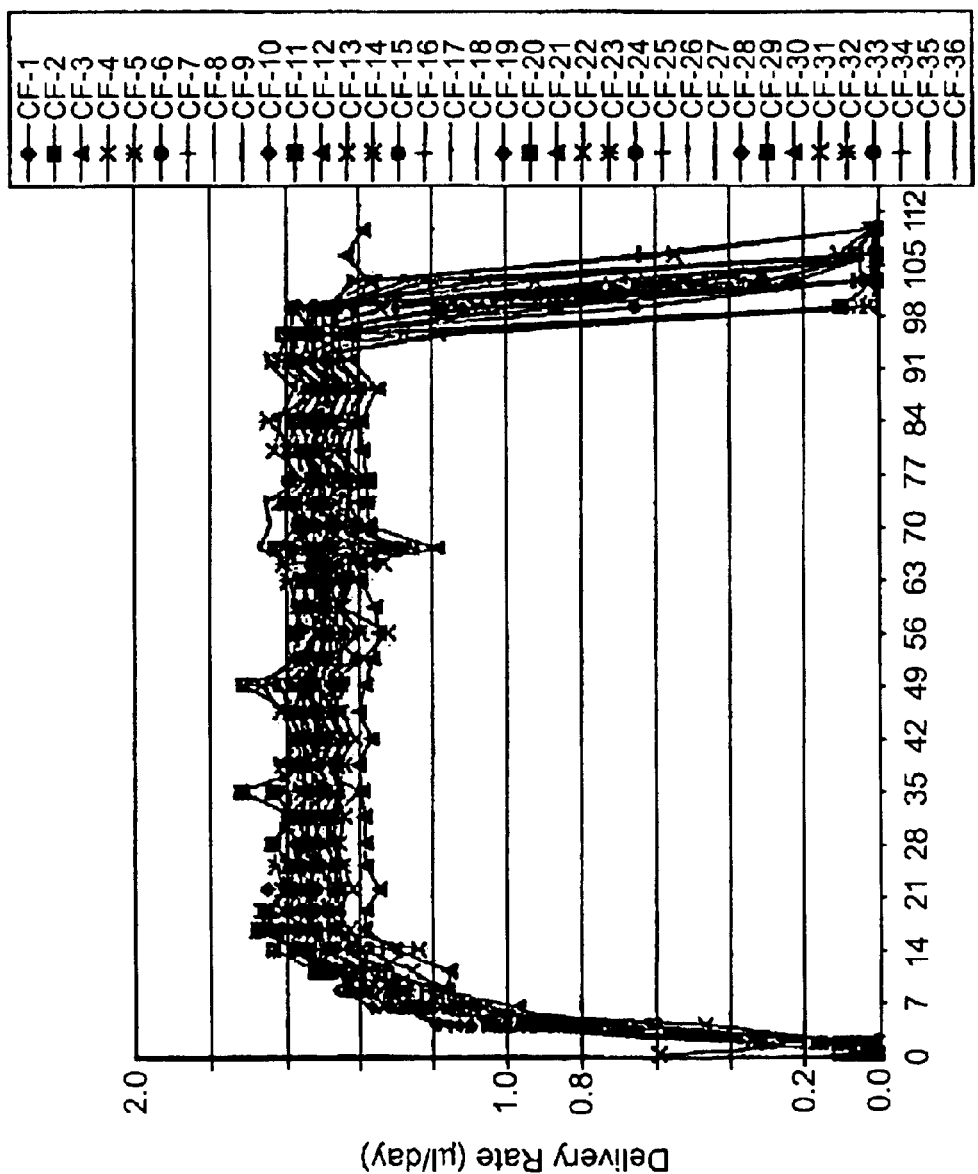
FIG. 9 relates to EXAMPLE 5 and shows in vitro release-rate data for drug delivery device comprising an osmotic pump system using the embodiment as shown in FIG. 8.
Figure 10:
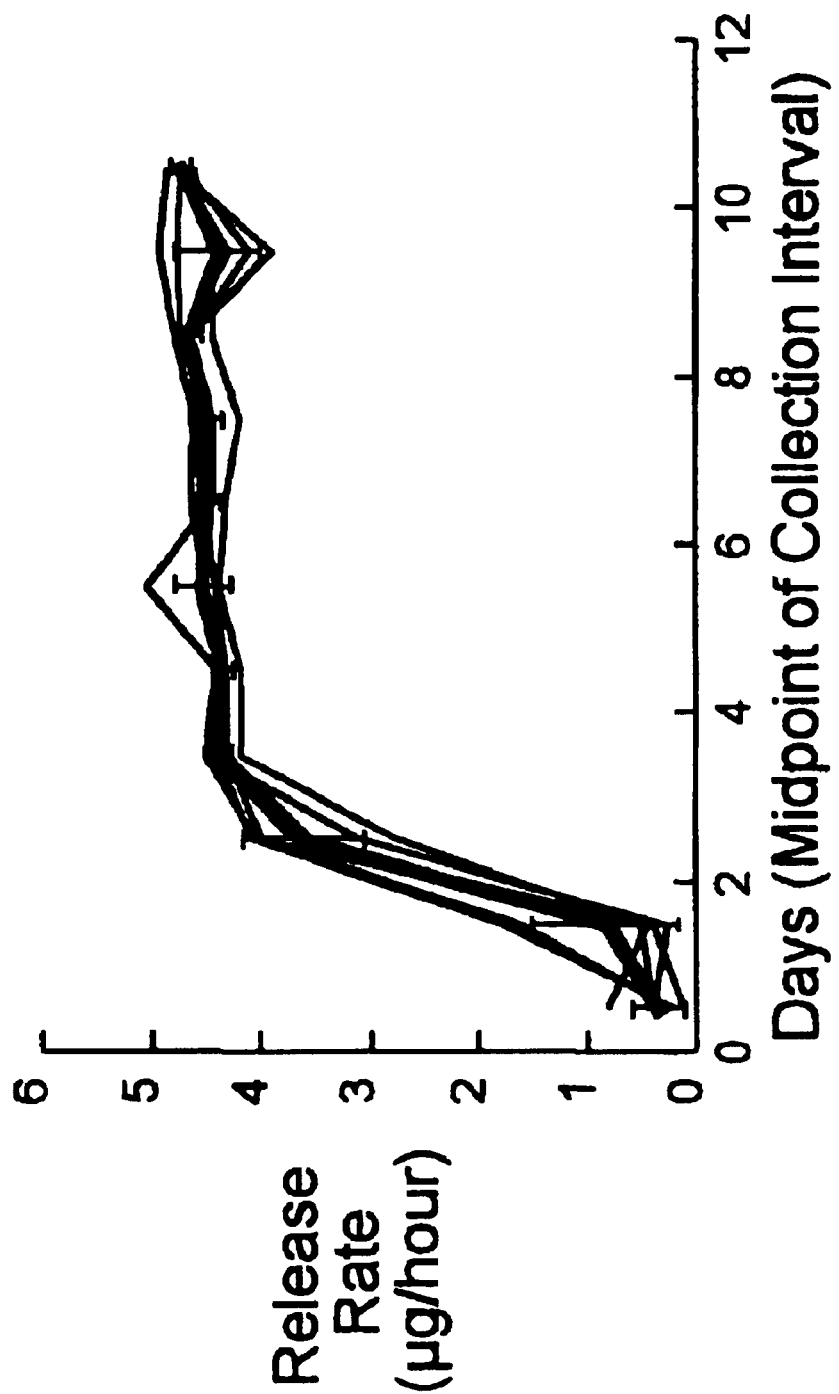
FIG. 10 relates to EXAMPLE 5 and shows sufentanil (µg/hour) released in vitro plotted against collection interval. Thin lines represent data from each of six individual devices. The thick line indicates the mean value; error bars represent standard deviations (SD).

The results (showing delivery rate (microliters per day) vs. time (days)) are shown in FIG. 9. As can be seen, the device dispensed about 1.5 microliters per hour, with approximately zero order kinetics, for over 100 days.

Example 6

Transition from Transdermal Fentanyl Patch to Delivery of Sufentanil Using Implant In another example the drug delivery device comprises an osmotic pump and is fitted with a plug defining a flow pathway as shown in FIG. 7. This drug delivery device of this example was employed in a study in which users of the Duragesico® patch (fentanyl transdermal patch) were converted to the implanted system of the invention which delivers sufentanil for six weeks.

The sufentanil delivery rates for this study were 10 micrograms per hour (at a concentration of 104.4 milligrams per ml) and 20 micrograms per hour (at a concentration of 208.7 milligrams per ml).

The strategy employed to select and implant a device comprising a pump that delivers an appropriate dose was as follows: 1: If a patient is not already using Duragesic (transdermal fentanyl, Janssen) as their primary opioid, transition the patient from present opioids to Duragesic (according to usual clinical practice, over a six-to-nine day period). 2: Once the Duragesic dose is stable and comprises 70% of daily opioid consumption, convert the patient's fentanyl dose to a sufentanil dose based on a 1:7.5 potency ratio. 3: Implant a drug delivery device into a patient which provides the appropriate dosage. 4: Continue Duragesic for one patch cycle until drug delivery is initiated from the drug delivery device.

The methods employed were as follows:

A conversion protocol was devised to allow easy conversion of patients from their previous opioid medication to sufentanil implants. The strategy generally followed the steps: 1) Quantify present opioids as "oral morphine equivalents." 2) Apply appropriate Duragesic® patch. 3) Titrate Duragesic® dose till stable. 4) Convert fentanyl dose to sufentanil dose. 5) Implant a device containing sufentanil. The following conversion table was produced:

| Duragesic ® (μg/hr) | Equivalent Invention delivery rate ™ (μg/hr) |
| --- | --- |
| 25 | 3.3 |
| 50 | 6.7 |
| 75 | 10.0 |
| 100 | 13.3 |

Eighteen patients with chronic pain of various etiologies provided informed consent to participate in the study. All patients were receiving Duragesic, 75 μg/hr or 150 μg/hr, as their primary opioid (70% of daily opioid intake) and had stable opioid intake (defined, in part, as no change in Duragesic dose in the previous month). Patients underwent screening for 1–3 weeks to quantify and establish stability of opioid intake and pain VAS (Visual Analysis Scale) scores (0–10 cm). Based on the relative potency of fentanyl and sufentanil being 1:7.5, patients received implants of the invention delivering 10 or 20 μg/hr sufentanil, respectively. The implant was placed subcutaneously, just above the elbow, on an outpatient basis using local anesthesia and a specially-designed implanter.

During the three-day startup period of the osmotic system, analgesia was provided by continuing the patient's Duragesic therapy. After drug delivery approaches steady state, Duragesic was discontinued and the patient used short-acting opioids, typically oxycodone, to treat breakthrough pain. Opioid intake and VAS score were recorded daily during the six-week implant period. The primary efficacy endpoint was evaluated at day 28 of the implant period. Outcome was based on a change in VAS score and successful replacement of previous opioid use. VAS score was categorized as improved (>20% decrease), worse (>20% increase), or unchanged.

The sufentanil dose was considered correct for that patient if: a) the patient showed no signs of opioid overdose during treatment, particularly during the period during which drug delivery approached steady state, and, b) if treatment was associated with substantial replacement of previous opioid therapy. Replacement of previous opioid therapy was quantified from the patient's total daily breakthrough opioid medication during treatment and their total daily opioid dose during screening; all opioids were quantified as "oral morphine equivalents" (OME) based on conversion values from the Opioid Conversion Calculator (Cynergy Group, Poulsbo, Wash.). At the end of the implant period (no more than 6 weeks of treatment), the implanted drug delivery device of the invention was explanted under local anesthesia, previous opioid therapy was resumed, and patient global preference was assessed.

Results were as follows: Both the implantation and explantation procedure was well tolerated by the patient. No patient demonstrated signs of overdose during the implant period. Median opioid replacement was 72%; opioid replacement exceeded 50% in 78% of patients. Pain VAS scores improved or were unchanged in 78% of patients. Sixty-one percent of patients preferred the implanted device or had no preference. The results are summarized in the following tables.

| Opioid Replacement (At Day 28). | |
| --- | --- |
| Number of patients | Opioid Replacement* |
| 14 | >50% |
| 2 | 20–50% |
| 2 | <20% |

*Opioid replacement is defined as 100% - (Duragesic opioid intake during treatment)/(Total opioid intake during screening)

| Pain VAS Score At Day 28 Of Therapy. | |
| --- | --- |
| Pain VAS Score | Number of patients |
| Improved* | 6 |
| No change | 8 |
| Worse† | 4 |

*Improved: 20% decrease in pain VAS score
† Worse: 20% increase in pain VAS score

| Patient Global Preference After Completion Of Therapy. | |
| --- | --- |
| Patient preference | Number of patients |
| "Very much prefer implant" | 7 |
| "Prefer implant" | 2 |
| "No preference" | 2 |
| "Prefer previous therapy" | 5 |
| "Much prefer previous therapy" | 2 |

In conclusion, the absence of signs of opioid overdose and the large replacement of previous opioid therapy by the implant of the invention indicate that the potency ratio used in the dose selection/transition strategy is appropriate. The patient preference rating shows that more patients prefer the implant than prefer the previous therapy.

Example 7

Pharmacokinetic Characteristics of the Implant System

A major concern in the use of implanted device to deliver potent drugs such as fentanyl and fentanyl congeners focuses on changes in the environment of use—that is, in the body of the subject—that could affect delivery rate and the amount of drug delivered. Where a drug as potent as fentanyl or a fentanyl congener is administered, even a very minute change in the delivery profile can have severe effects on the subject, including over-dose with attendant side effects such as respiratory depression and even death. Of particular concern are unpredictable and unexpected fluctuations in body temperature, such as those associated with fever often experienced with a flu or other illness. These concerns are even more serious where the drug is to be delivered through use of an implant that contains a highly concentrated formulation of the drug which cannot be readily removed from the body or where the delivery rated cannot be readily adjusted (e.g., where the implant is a fixed delivery rate device).

This example was designed to consider this issue in the context of the present invention. The study was conducted to determine the half-life at which the fentanyl congener sufentanil is absorbed from the subcutaneous space, bioavailability of sufentanil, and the impact of induced fever on the plasma concentration (Cp) of sufentanil. It is known that a fever would increase the temperature of the housing of the implanted drug delivery device therefore causing thermal expansion of the formulation, and thereby releasing a small bolus of sufentanil. An experiment was conducted to assess the impact on plasma concentration of sufentanil released from an exemplary drug delivery device of the invention in normal human subjects in the event of a temperature rise associated with a typical fever in humans. If the extra bolus of drug released from the drug delivery device of the invention as a result of thermal expansion of the formulation was found to be absorbed rapidly into the systemic circulation as indicated by the blood plasma concentration of drug (i.e., the absorption half-life is short), then the methods and devices taught by this invention would have more limited use in patients who are not monitored by health care givers due to safety concerns. If, however, the drug formulation released as a result of thermal expansion is more slowly absorbed (i.e., the absorption half-life is long), then a typical fever experienced by a patient using the device of this invention would not pose a safety concern to the patient and would therefore make the device and methods of this invention a more practical and convenient way to treat pain.

The drug delivery device used in this example included an osmotic pump and a thermal expansion element comprising a plug as shown in FIG. 7 containing a formulation of sufentanil at a concentration of about 109 mg/ml and designed to deliver a dosage of 5 micrograms of sufentanil per hour. Based on the thermal expansion coefficient of the drug formulation, it is expected that a "typical" fever of 2.5° C. should release approximately six hours of formulation. Methods were as follows: 1) Consent was obtained from twelve healthy opioid-naive volunteers (six males) aged 19–38 years. Subjects received the opioid antagonist drug naltrexone, 50 mg orally twice daily, to prevent opioid-related effects. 2) Drug Administration: On day 0, subjects received a solution of sufentanil citrate, 10 µg/hour, intravenously (IV) for six hours to establish a reference to establish the bioavailability of sufentanil. On day 2, the drug delivery device described above was implanted in the medial aspect of the upper arm under local anesthesia. On day 11, the drug delivery device was explanted. 3) Fever induction: On day 9, half of the subjects received aldesleukin (interleukin-2, Chiron), 150,000–250,000 IU, to induce a experimental fever of about 2.5° C. 4) Blood sampling: Approximately 50 venous blood samples were taken from each subject, starting before the IV infusion and ending on day 14. 5) Assay: Sufentanil concentrations in plasma (Cp) were measured using a specific MS-LC-LC assay sensitive to 2 pg/ml (CV<9% at that concentration).

Pharmacokinetic modeling: A population analysis was performed using nonlinear mixed effects modeling (NONMEM). Initially, systemic pharmacokinetics (2-vs. 3-compartment models) were estimated based on the IV dose of sufentanil. Absorption from the drug delivery device was then modeled as a first-order process (based on all data, except those during induced fever). Release rate was modeled as a linear spline with four knots. The first and fourth knots were positioned at time of implant and explant, respectively. The height of all knots and the time of the two intermediate knots were estimated. Cumulative release over the implant period was calculated from the post hoc (individual) estimates of the release rate profiles and compared by unpaired t-test to the cumulative in vitro release of implant systems from the same manufacturing lot.

Figure 11:
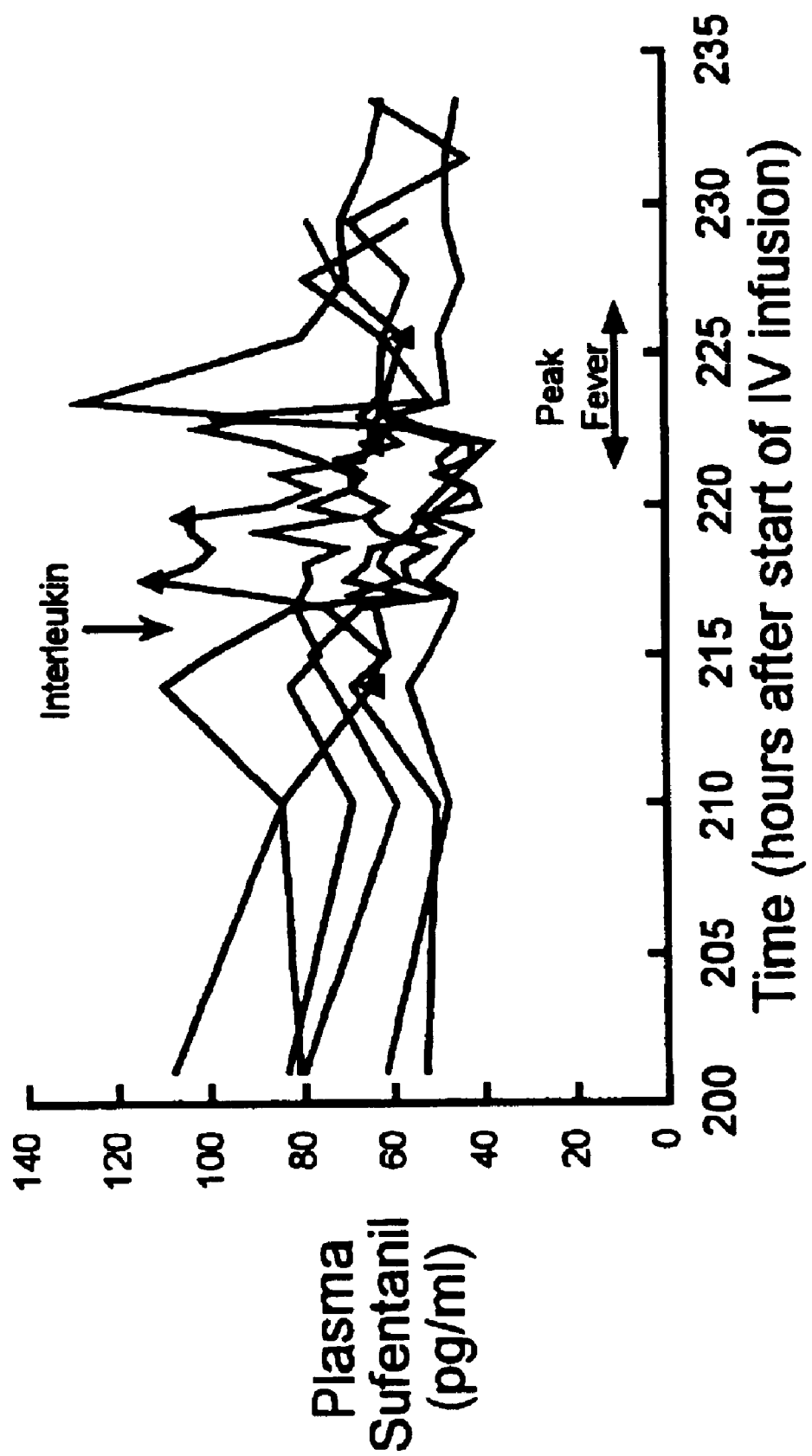
FIG. 11 relates to EXAMPLE 7 and shows plasma concentrations of sufentanil before and during induction of experimental fever are shown. Each line represents data from an individual human subject.

Results show that absorption half-life of sufentanil was 16.2 hours, and it appears that fever was not associated with an undesirable systemic increase of sufentantil as indicated by blood plasma concentrations. Results are shown graphically, in FIG. 11.

The absorption half-life of sufentanil is far longer than that typically associated with intramuscular administration of large volumes of dilute solutions of opioids; this may result from the small volume administered or the viscosity of the highly concentrated benzyl alcohol solution. This lengthy half-life is desirable—it dampens changes in Cp if physiologic conditions such as fever alter release from the drug delivery device. This may partly explain why fever does not increase sufentanil Cp systematically; a second factor is that fever causes physiologic changes such as increases in cardiac output that may counteract the increased delivery rate. The foregoing example show the unexpected result that the methods and devices of the present invention can be used as a safe and convenient way to treat pain even when there is unexpected fluctuations in the overall body temperature of a patient such as due to fever.

Example 8

Delivery of Sufentanil from Implant—Plasma Levels Over a Delivery Period of Approximately 45 Days A study was conducted to determine in vivo (human) sufentanil plasma concentrations produced by an implanted drug delivery device of the invention over a period of about 45 days. The study employed devices having an osmotic pump with a thermal expansion element comprising a plug as shown in FIG. 7 containing a formulation of sufentanil, which devices were designed to deliver sufentanil at doses of 5, 10 or 20 micrograms per hour. A number of informed consenting patients were selected for the study. Each patient was implanted with one or two of the drug delivery devices as described above in order to administer the appropriate dosage of drug to the patient. Thus, the patients in the study received a variety of doses of sufentanil via implanted drug delivery devices ranging from 5–40 micrograms per hour. The plasma levels of sufentanil of all patients in the study were measured over a period of about 45 to 50 days.

Figure 12:
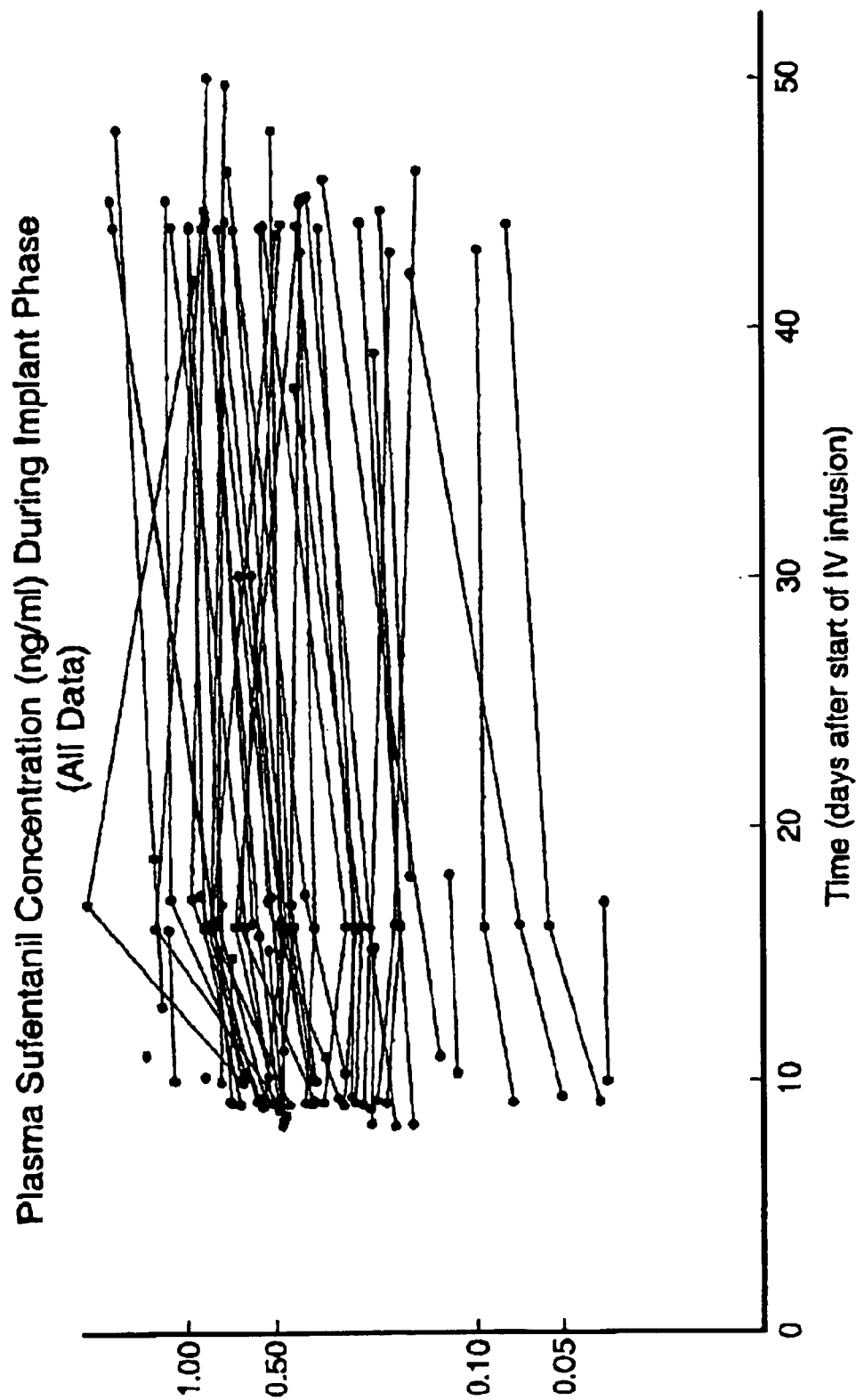
FIG. 12 is a graph showing plasma sufentanil concentration following implantation.

FIG. 12 shows the plasma concentration in ng/ml in a number of the human patients. The y-axis of this graph is shown as a log scale. Each line represents an individual subject. The graph shows that the plasma concentration of sufentanil as delivered from the drug delivery devices was at a steady rate (near zero order kinetics) throughout the study, and that the average plasma level varies between about 0.05 and 1.00 ng/ml. The variability of the plasma concentration of sufentanil between individual patients resulted mostly from the fact that the patients in the study received differing dosages of sufentanil from each other depending on each individual's identified dosage requirement.

Figure 13:
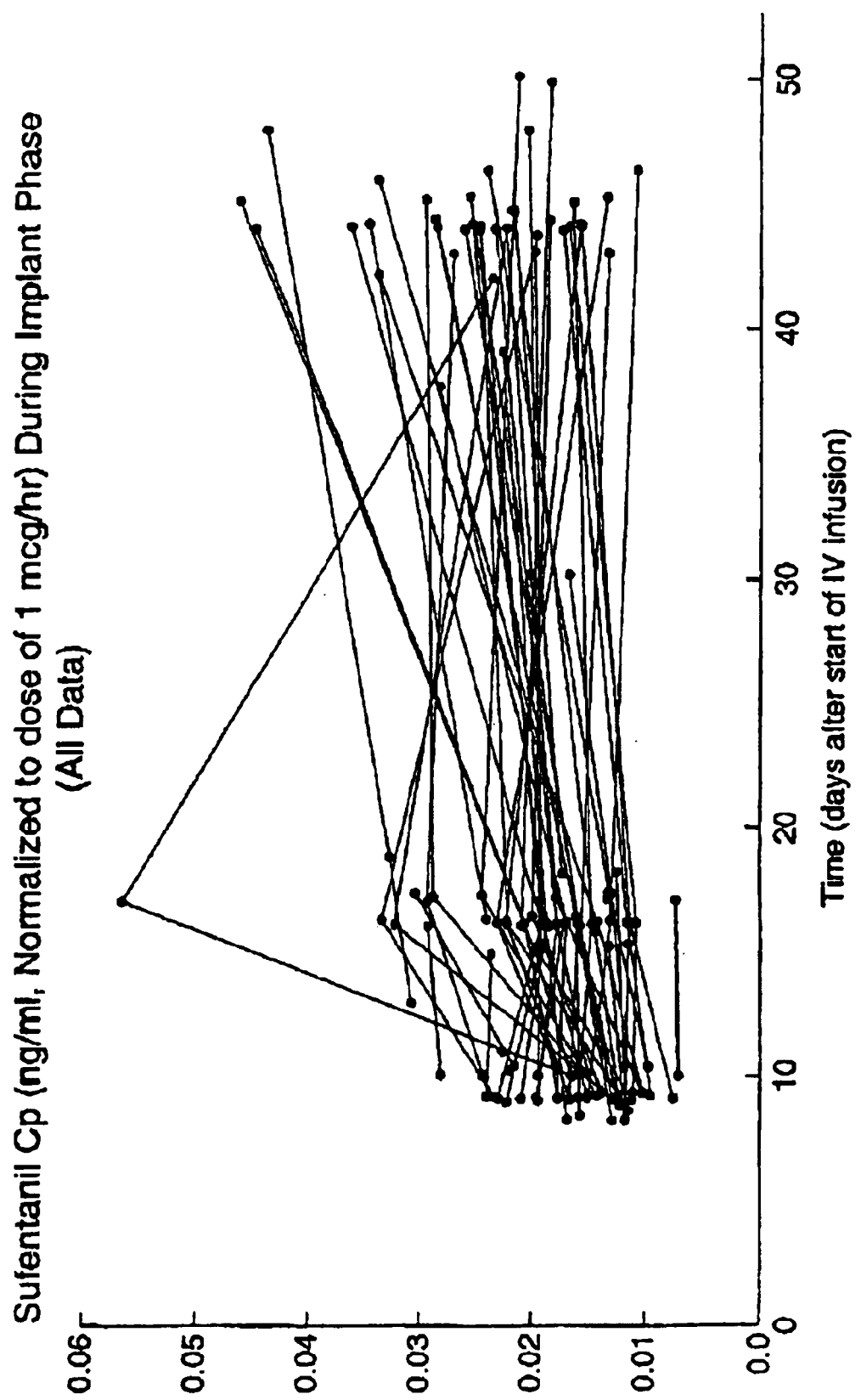
FIG. 13 is a graph showing sufentanil plasma concentration (Cp), normalized to a dose 1 microgram/hr following implantation.

FIG. 13 shows the plasma concentration in ng/ml in a number of human subjects. The data has been normalized to a dose of 1 microgram/hr. The y-axis of this graph is shown as a linear scale. Each line represents an individual subject. The graph shows that plasma concentration of sufentanil in a given individual was relatively constant throughout the study, and that the average plasma level varies between about 0.01 and 0.04 ng/ml for this normalized set.

This study supports that the rate of release of sufentanil is steady and within a desired therapeutic range when the drug delivery device of the invention is implanted in vivo over a period of about 45 days.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A controlled drug delivery device, adapted for whole implantation in a subject, the device comprising:

a housing defining a reservoir, the reservoir containing a formulation comprising a drug selected from the group consisting of fentanyl or a fentanyl congener, wherein the drug is present in an amount sufficient for treatment of pain in a subject for a period of at least about 3 days;

a pump operatively connected to the housing; and a thermal expansion element comprising an inlet, a thermal expansion channel adapted to contain a volume of formulation associated with thermal expansion, and an outlet;

wherein in use, the inlet, thermal expansion channel, and outlet define a flow pathway from the reservoir and out of the device such that actuation of the pump effects movement of formulation through the flow pathway.

2. The device of claim 1, wherein the flow pathway of the thermal expansion element is at least partially defined by a plug seated within the housing.

3. The device of claim 1, wherein the flow pathway of the thermal expansion element is at least partially defined by a plug seated within the housing, and an inner wall of the housing.

4. The device of claim 1, wherein the thermal expansion element comprises a valve positioned and adapted for maintaining a sealed reservoir until opened.

5. The device of claim 4, wherein the thermal expansion element comprises a plunger, wherein at least a portion of the plunger is slidably positioned within the flow pathway and seated within the valve such that when in a closed position the plunger and valve occlude the flow pathway to prevent movement of formulation out of the outlet.

6. The device of claim 1, wherein the flow pathway narrows from a wider inlet and thermal expansion channel to a narrower outlet.

7. The device of claim 1, wherein the device is adapted for delivery of drug at a rate of from about 0.01 micrograms per hour to 2000 micrograms per hour.

8. The device of claim 1, wherein said drug is present in a concentration of about 5 mg/mL to about 400 mg/mL.

9. The device of claim 1, wherein the drug is sufentanil.

10. A method of treating pain in a subject, the method comprising the steps of:

wholly implanting at an implantation site in a subject the drug delivery device of claim 1; and parenterally delivering the formulation from the drug delivery device to the subject so that drug enters the systemic circulation and is transported thereby to a site of action in an amount sufficient to treat pain.

11. The method of claim 10, wherein the thermal expansion element of the device comprises a valve and a plunger, at least a portion of the plunger being slidably positioned within the flow pathway and seated within the valve such that when in a closed position the plunger and valve occlude the flow pathway to prevent movement of formulation past the thermal expansion channel in a direction toward the outlet, and wherein the method further comprises the step of actuating the plunger so as to open the valve prior to said implanting.

12. The method of claim 10, wherein the drug delivery device is implanted at a subcutaneous site.

13. The method of claim 10, wherein the formulation is delivered at a volume rate of from about 0.01 μl/day to 2 ml/day.

14. The method of claim 10, wherein drug is delivered at a rate of from about 0.01 μg per hour to 2,000 μg per hour.

15. The method of claim 10, wherein the drug is sufentanil.

16. The method of claim 10, wherein said delivering is for a period of from about 4 weeks to 12 months.

17. The method of claim 10, wherein the device comprises an amount of drug sufficient to provide for alleviation of pain in the subject for a period of more than 30 days.

18. A controlled drug delivery device, adapted for whole implantation in a subject, the device comprising:
   a housing defining a reservoir, the reservoir containing a formulation comprising sufentanil in an amount sufficient for treatment of pain in a subject for a period of at least about 3 days;
   a pump operatively connected to the housing; and
   a thermal expansion element comprising an inlet, a thermal expansion channel adapted to contain a volume of formulation associated with thermal expansion, and a delivery outlet;
   wherein in use, the inlet, thermal expansion channel, and outlet define a flow pathway from the reservoir and out of the device such that actuation of the pump effects movement of formulation through the flow pathway.

19. The device of claim 18, wherein the flow pathway of the thermal expansion element is at least partially defined by a plug seated within the housing.

20. The device of claim 18, wherein the flow pathway of the thermal expansion element is at least partially defined by a plug seated within the housing, and an inner wall of the housing.

21. The device of claim 18, wherein the thermal expansion element comprises a valve.

22. The device of claim 18, wherein the thermal expansion element comprises a plunger, wherein at least a portion of the plunger is slidably positioned within the flow pathway and seated within the valve such that when in a closed position the plunger and valve occlude the flow pathway to prevent movement of formulation through the outlet.

23. The device of claim 18, wherein said drug is present in a concentration of about 50 mg/mL to about 400 mg/mL.

24. A method of treating pain in a subject, the method comprising the steps of:
   wholly implanting at an implantation site in a subject the drug delivery device of claim 18; and
   parenterally delivering the formulation from the drug delivery device to the subject so that drug enters the systemic circulation and is transported thereby to a site of action in an amount sufficient to treat pain.

25. The method of claim 23, wherein the drug delivery device is implanted at a subcutaneous site.

26. The method of claim 23, wherein the formulation is delivered at a volume rate of from about 0.01 μl/day to 2 ml/day.

27. The method of claim 23, wherein the device comprises an amount of drug sufficient to provide for alleviation of pain in the subject for a period of more than 30 days.

* * * * *